US009498536B2

(12) United States Patent
Mousa et al.

(10) Patent No.: US 9,498,536 B2
(45) Date of Patent: *Nov. 22, 2016

(54) METHOD AND COMPOSITION OF THYROID HORMONE ANALOGUES AND NANOFORMULATIONS THEREOF FOR TREATING ANTI-INFLAMMATORY DISORDERS

(71) Applicant: NANOPHARMACEUTICALS LLC, Rensselaer, NY (US)

(72) Inventors: Shaker A. Mousa, Wynantskill, NY (US); Paul J. Davis, West Sand Lake, NY (US)

(73) Assignee: NANOPHARMACEUTICALS LLC, Rensselaer, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/242,041

(22) Filed: Apr. 1, 2014

(65) Prior Publication Data

US 2014/0294931 A1    Oct. 2, 2014

Related U.S. Application Data

(63) Continuation-in-part of application No. 12/816,287, filed on Jun. 15, 2010, now Pat. No. 9,220,788, which is a continuation-in-part of application No. 12/947,389, filed on Nov. 16, 2010, now Pat. No.

(Continued)

(51) Int. Cl.

| A61K 47/48 | (2006.01) |
|---|---|
| A61K 31/192 | (2006.01) |
| A61K 9/51 | (2006.01) |
| A61K 45/06 | (2006.01) |
| A61K 31/4412 | (2006.01) |
| A61K 31/05 | (2006.01) |
| A61K 31/573 | (2006.01) |

(Continued)

(52) U.S. Cl.
CPC ........... *A61K 47/482* (2013.01); *A61K 9/5031* (2013.01); *A61K 9/5153* (2013.01);

(Continued)

(58) Field of Classification Search
None
See application file for complete search history.

(56) References Cited

U.S. PATENT DOCUMENTS 3,625,214 A   12/1971 Higuchi
4,205,058 A   5/1980 Wagner et al.
(Continued)

FOREIGN PATENT DOCUMENTS

CA    2673133 A1   11/2008
CN    1126589       7/1996
(Continued)

OTHER PUBLICATIONS

J Wood, K Bonjean, S Ruetz, A Bellahcene, L Devy, JM Foidart, V Castronovo, JR Green. "Novel Antiangiogenic Effects of the Bisphosphonate Compound Zoledronic Acid." The Journal of Pharmacology and Experimental Therapeutics, vol. 302, No. 3, 2002, pp. 1055-1061.*

(Continued)

*Primary Examiner* — Isaac Shomer
(74) *Attorney, Agent, or Firm* — Schmeiser, Olsen & Watts, LLP

(57) ABSTRACT

Thyroid hormone antagonists and their nanoparticle formulations (Nanotetrac™ or Nanotriac™) act at a cell surface receptor to block angiogenesis and tumor cell proliferation. The complex anti-angiogenic performs actions on specific cytokines and chemokines. Thyroid hormone antagonists inhibit expression in tumor cells of cytokine genes, e.g., specific interleukins, and chemokine genes, such as fractalkine (CX3CL1), and chemokine receptor genes (CX3CR1) that are targets in the development of inflammation-suppressant drugs. This application discloses a novel composition of Tetra or Tri-iodothyroacetic acid (tetrac or triac), other thyroid partial agonists or antagonists and their nanoparticle formulations conjugated to polymers and encapsulating non-steroidal anti-inflammatory, anti-inflammatory glucocorticoids, and/or polyphenols for the management of various acute and chronic inflammatory disorders ranging from neurological, vascular, and musculoskeletal disorders.

23 Claims, 4 Drawing Sheets

Related U.S. Application Data 9,289,395, which is a continuation of application No. 12/004,979, filed on Dec. 21, 2007, now abandoned, which is a continuation-in-part of application No. 14/185,010, filed on Feb. 20, 2014, which is a continuation of application No. 11/786,723, filed on Apr. 11, 2007, now Pat. No. 8,668,926, which is a continuation-in-part of application No. 11/663,047, filed on Sep. 15, 2005, now Pat. No. 8,071,134.

(60) Provisional application No. 61/807,123, filed on Apr. 1, 2013, provisional application No. 61/187,799, filed on Jun. 17, 2009, provisional application No. 61/219,993, filed on Jun. 24, 2009, provisional application No. 61/222,289, filed on Jul. 1, 2009, provisional application No. 61/237,178, filed on Aug. 26, 2009, provisional application No. 61/327,909, filed on Apr. 26, 2010, provisional application No. 60/876,770, filed on Dec. 22, 2006, provisional application No. 60/922,113, filed on Apr. 5, 2007, provisional application No. 60/936,223, filed on Jun. 18, 2007, provisional application No. 60/959,006, filed on Jul. 9, 2007, provisional application No. 60/967,016, filed on Aug. 30, 2007, provisional application No. 60/994,895, filed on Sep. 21, 2007, provisional application No. 61/000,262, filed on Oct. 23, 2007, provisional application No. 61/003,935, filed on Nov. 20, 2007.

(51) Int. Cl.
*A61K 31/60* (2006.01)
*A61K 9/50* (2006.01)

(52) U.S. Cl.
CPC ............ *A61K 31/05* (2013.01); *A61K 31/192* (2013.01); *A61K 31/4412* (2013.01); *A61K 31/573* (2013.01); *A61K 31/60* (2013.01); *A61K 45/06* (2013.01); *A61K 47/4823* (2013.01); *A61K 47/48176* (2013.01); *A61K 47/48215* (2013.01); *A61K 47/48315* (2013.01); *Y10S 977/773* (2013.01); *Y10S 977/906* (2013.01)

(56) References Cited

U.S. PATENT DOCUMENTS

| | | |
|---|---|---|
| 4,650,751 A | 3/1987 | Siegel et al. |
| 4,789,734 A | 12/1988 | Pierschbacher |
| 4,801,504 A | 1/1989 | Burdick et al. |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,158,978 A | 10/1992 | Rubin |
| 5,225,204 A | 7/1993 | Chen et al. |
| 5,231,000 A | 7/1993 | Majocha et al. |
| 5,304,121 A | 4/1994 | Sahatjian |
| 5,410,016 A | 4/1995 | Hubbell et al. |
| 5,438,126 A | 8/1995 | DeGroot et al. |
| 5,449,665 A | 9/1995 | Sollevi |
| 5,482,719 A | 1/1996 | Guillet et al. |
| 5,571,840 A | 11/1996 | Mayor et al. |
| 5,591,709 A | 1/1997 | Lindenbaum |
| 5,593,688 A | 1/1997 | Baldeschwieler |
| 5,648,506 A | 7/1997 | Desai et al. |
| 5,733,871 A | 3/1998 | Alps et al. |
| 5,766,635 A | 6/1998 | Spenleuhauer et al. |
| 6,013,641 A | 1/2000 | Lussow et al. |
| 6,139,870 A | 10/2000 | Verrecchia |
| 6,316,412 B1 | 11/2001 | Ginsberg et al. |
| 6,414,037 B1 | 7/2002 | Pezzuto et al. |
| 6,482,406 B1 | 11/2002 | Stewart |
| 6,515,100 B2 | 2/2003 | Harris |
| 6,534,676 B2 | 3/2003 | Morkin et al. |
| 6,677,473 B1 | 1/2004 | Madison et al. |
| 6,740,680 B1 | 5/2004 | Danforth, Jr. et al. |
| 6,818,620 B2 | 11/2004 | Bhatnagar |
| 6,821,947 B2 | 11/2004 | Iozzo |
| 6,936,274 B2 | 8/2005 | Hanshew, Jr. |
| 7,166,155 B2 | 1/2007 | Ishikawa |
| 7,358,085 B2 | 4/2008 | Zhang et al. |
| 7,638,558 B2 | 12/2009 | Breitenkamp et al. |
| 7,785,632 B2 * | 8/2010 | Mousa ................. A61K 31/198 424/489 |
| 7,807,621 B2 | 10/2010 | Mazar et al. |
| 8,026,209 B2 | 9/2011 | Gaillard et al. |
| 8,071,134 B2 | 12/2011 | Mousa et al. |
| 8,242,171 B2 | 8/2012 | Sinclair et al. |
| 8,518,451 B2 | 8/2013 | Mousa et al. |
| 8,668,926 B1 * | 3/2014 | Mousa et al. ................. 424/450 |
| 8,802,240 B2 * | 8/2014 | Davis ............... A61K 39/39533 428/450 |
| 9,180,107 B2 * | 11/2015 | Lin ....... A61K 31/192 |
| 9,198,887 B2 * | 12/2015 | Mousa ................. A61K 31/704 |
| 9,220,788 B2 * | 12/2015 | Davis ................. A61K 41/0038 |
| 9,272,049 B2 | 3/2016 | Alexander-Bridges et al. |
| 9,289,395 B2 | 3/2016 | Davis et al. |
| 2001/0021763 A1 | 9/2001 | Harris |
| 2001/0023254 A1 * | 9/2001 | McElroy ....................... 514/439 |
| 2001/0046521 A1 | 11/2001 | Zasloff et al. |
| 2002/0049247 A1 | 4/2002 | Chen |
| 2002/0132005 A1 * | 9/2002 | Faour ........................... 424/473 |
| 2002/0137676 A1 | 9/2002 | Hsiang et al. |
| 2002/0151594 A1 | 10/2002 | Morkin et al. |
| 2003/0027940 A1 | 2/2003 | Lang et al. |
| 2003/0138557 A1 | 7/2003 | Allison |
| 2003/0157098 A1 | 8/2003 | Laug |
| 2003/0162758 A1 | 8/2003 | Schwartz et al. |
| 2003/0165576 A1 | 9/2003 | Fujii et al. |
| 2004/0013728 A1 | 1/2004 | Oh et al. |
| 2004/0033259 A1 | 2/2004 | Hanshew, Jr. et al. |
| 2005/0124862 A1 * | 6/2005 | Mousa et al. ................. 600/300 |
| 2005/0158376 A1 | 7/2005 | Sardi et al. |
| 2005/0171027 A1 | 8/2005 | Sinclair et al. |
| 2005/0222387 A1 | 10/2005 | Debatin et al. |
| 2005/0249721 A1 | 11/2005 | Houston et al. |
| 2005/0272817 A1 | 12/2005 | Heino |
| 2006/0166303 A1 * | 7/2006 | Spanuth ......................... 435/25 |
| 2006/0210539 A1 | 9/2006 | Zhang |
| 2006/0216251 A1 * | 9/2006 | Morariu ........................ 424/59 |
| 2007/0117841 A1 * | 5/2007 | Ozes et al. ..................... 514/310 |
| 2007/0190160 A1 | 8/2007 | Turos et al. |
| 2008/0081074 A1 * | 4/2008 | Gu .............. A61K 9/5153 424/489 |
| 2008/0124280 A1 * | 5/2008 | Mousa et al. ................. 424/9.3 |
| 2008/0193377 A1 | 8/2008 | Line et al. |
| 2008/0199850 A1 * | 8/2008 | Sutter ............... G01N 33/5023 435/4 |
| 2009/0022806 A1 * | 1/2009 | Mousa et al. ................. 424/489 |
| 2009/0175862 A1 | 7/2009 | Silverio et al. |
| 2010/0112079 A1 | 5/2010 | Mousa et al. |
| 2010/0159021 A1 * | 6/2010 | Davis et al. ................... 424/499 |
| 2010/0209382 A1 | 8/2010 | Alexander-Bridges et al. |
| 2010/0255108 A1 | 10/2010 | Lin et al. |
| 2011/0052715 A1 * | 3/2011 | Davis et al. ................... 424/499 |
| 2011/0142941 A1 * | 6/2011 | Davis et al. ................... 424/489 |
| 2012/0258069 A1 | 10/2012 | Alexander-Bridges et al. |
| 2012/0315320 A1 | 12/2012 | Davis et al. |
| 2014/0072635 A1 | 3/2014 | Mousa et al. |
| 2014/0072646 A1 | 3/2014 | Mousa et al. |
| 2014/0199375 A1 | 7/2014 | Fein et al. |

FOREIGN PATENT DOCUMENTS

| | | |
|---|---|---|
| WO | 9500135 | 1/1995 |
| WO | 9640048 | 12/1996 |
| WO | 9833942 | 8/1998 |

(56) References Cited

FOREIGN PATENT DOCUMENTS

| | | |
|---|---|---|
| WO | 9856771 | 12/1998 |
| WO | 9958119 A1 | 11/1999 |
| WO | 9959548 A1 | 11/1999 |
| WO | 9962549 | 12/1999 |
| WO | 0064431 A1 | 11/2000 |
| WO | 0078815 A1 | 12/2000 |
| WO | 0113031 A2 | 2/2001 |
| WO | 0113936 A1 | 3/2001 |
| WO | 0176589 A1 | 10/2001 |
| WO | 0203914 A2 | 1/2002 |
| WO | 0249501 A2 | 6/2002 |
| WO | 02060389 A2 | 8/2002 |
| WO | 03075741 A2 | 9/2003 |
| WO | 2004013728 A2 | 2/2004 |
| WO | 2004069201 A2 | 8/2004 |
| WO | 2005027895 A2 | 3/2005 |
| WO | 2006003014 A2 | 1/2006 |
| WO | 2006031922 A2 | 3/2006 |
| WO | 2007035612 A2 | 3/2007 |
| WO | 2008051291 A2 | 5/2008 |
| WO | 2008140507 A2 | 11/2008 |
| WO | 2010120506 A2 | 10/2010 |
| WO | 2010148007 A2 | 12/2010 |

OTHER PUBLICATIONS

M Yalcin, DJ Bharali, L Lansing, E Dyskin, SS Mousa, A Hercbergs, FB Davis, PJ Davis, SA Mousa. "Tetraidothyroacetic Acid (Tetrac) and Tetrac Nanoparticles Inhibit Growth of Human Renal Cell Carcinoma Xenografts." Anticancer Research, vol. 29, 2009, pp. 3825-3832.*

*Kennecott Corporation*, PlaintiffAppellant, v. *Kyocera International, Inc. and Kyoto Ceramic Co., Ltd.*, DefendantAppellee. Case Decided Dec. 22, 1987. (https://law.resource.org/pub/us/case/reporter/F2/835/835.F2d.1419.871151.html), accessed Jan. 15, 2016, 5 printed pages.*

Sunwoo et al., "Novel Proteasome Inhibitor PS-341 Inhibits Activation of Nuclear Factor-KB, Cell Survival, Tumor Growth, and Angiogenesis in Squamous Cell Carcinoma", Clin. Cancer Res., 7:1419-1428 (2001) 10 pages.

Szatmari et al., "Detailed characterization of the mouse glioma 261 tumor model for experimental glioblastoma therapy", Cancer Sci., 97(6):546-553 (2006) 8 pages.

Szumiel, I., "Ca2+, Mg2+ and (Adenosine Diphosphate Ribose)n in Cellular Response to Irradiation", J. Theor. Biol., 101:441-451 (1983) 11 pages.

Takemaru et al., "Chibby, a nuclear β-catenin-associated antagonist of the Wnt/Wingless pathway", Nature, 422:905-909 (2003) 5 pages.

Tanaka et al., J. Soc. Gastroenterological Surgery, 27(2):360 (1996) 3 pages.

Tang et al., "Resveratrol-induced Cyclooxygenase-2 facilitates p53-dependent apoptosis in human breast cancer cells", Mol. Cancer Ther., 5(8):2034-2042 (2006) 9 pages.

Tang et al., "Thyroid Hormone Causes Mitogen-Activated Protein Kinase-Dependent Phosphorylation of the Nuclear Estrogen Receptor", Endocrinol., 145(7):3265-3272 (2004) 8 pages.

Tator et al., "Review of the secondary injury theory of acute spinal cord trauma with emphasis on vascular mechanisms", J. Neurosurg., 75(1):15-26 (1991) 13 pages.

Theodossiou et al., "Propylthiouracil-induced Hypothyroidism Reduces Xenograft Tumor Growth in Athymic Nude Mice", Cancer, 86:1596-1601 (1999) 6 pages.

Thompson et al., "The Clinical Manipulation of Angiogenesis: Pathology, Side-Effects, Surprises, and Opportunites with Novel Human Therapies." J. Pathol. 190(2000):330-337 8 pages.

Thraves et al., "Radiosensitization of Human Fibroblasts by 3-Aminobenzamide: An Inhibitor of Poly(ADP-Ribosylation)", Radiat Res., 104:119-127 (1985) 9 pages.

Tol et al., "Chemotherapy, Bevacizumab, and Cetuximab in Metastatic Colorectal Cancer", N. Engl. J. Med., 360 (6):563-572 (2009) 10 pages.

Tomanek et al., "A Thyroid Hormone Analog Stimulates Angiogenesis in the Post-infarcted Rat Heart", J. Mol. Cell Cardiol., 30(5):923-932 (1998) 10 pages.

Tomanek et al., "Angiogenesis: New Insights and Therapeutic Potential", Anatomical Record (New Anat.), 261:126-135 (2000) 10 pages.

Tomanek et al., "Early Coronary Angiogenesis in Resposne to Thyroxine: Growth Characteristics and Upregulation of Basic Fibroblast Growth Factor", Circ. Res., 82(5):587-593 (1998) 8 pages.

Tomanek et al., "Growth of the Coronary Vasculature in Hypertrophy: Mechanisms and Model Dependence", Cell. Mol. Bio. Res., 40(2):129-136 (1994) 8 pages.

Toms et al., "Thyroid Hormone Depletion Inhibits Astrocytoma Proliferation via a p53-Independent Induction of p21 (WAF/1CIP1)", Anticancer Res., 18:289-293 (1998) 5 pages.

Tuttle et al., "Recombinant Human TSH-Assisted Radioactive Iodine Remnant Ablation Achieves Short-Term Clinical Recurrence Rates Similar to Those of Traditional Thyroid Hormone Withdrawal", J. Nucl. Med., 49(5):764-770 (2008) 7 pages.

Tzirogiannis et al., "Enhanced Proliferation of Human Lung Adenocarcinoma and Small Cell Lung Carcinoma Cells Directed from the Cell Surface by Thyroid Hormone", in 89th Annual Meeting, The Endocrine Society (2007) Abstract Only 3 pages.

Utsumi et al., "Potentially Lethal Damage Versus Sublethal Damage: Independent Repair Processes in Actively Growing Chinese Hamster Cells", Radiat. Res., 77:346-360 (1979) 9 pages.

Van Waes et al., "Effects of the novel α□ integrin antagonist SM256 and cis-platinum on growth of murine squamos cell carcinoma PAM LY8", Int. J. Oncol., 16(6):1189-1195 (2000) 8 pages.

VanCutsem et al., "Cetuximab and Chemotherapy as Initial Treatment for Metastatic Colorectal Cancer", N. Engl. J. Med., 360:1408-1417 (2009) 10 pages.

Varnes et al., "The Effect of pH on Potentially Lethal Damage Recovery in A549 Cells", Radiat. Res., 108:80-90 (1986) 11 pages.

Velasco et al., "Dermatological Aspects of Angiogenesis." Brit. J. Dermatol. 147(2002):841-852 12 pages.

Wang et al., "DITPA stimulated bFGF, VEGF, angiopoietin, and Tie-2 and facilates coronary arteriolar growth", Am. J. Physiol. Heart Circ. Physiol., 284(2):H613-H618 (2003) 6 pages.

Wang et al., "Integrin-associated Protein Stimulates α2β1-dependent Chemotaxis via Gi-mediated inhibition of Adenylate Cyclase and Extracelular-regulated Kinases", J. Cell. Biol., 147:389-399 (1999) 11 pages.

Wen et al., "Prognostic Value of EGFR and TGF-α in Early Laryngeal Cancer Treated With Radiotherapy", Laryngoscope, 106(7):884-888 (1996) 6 pages.

Werdelin et al., "Neuropeptides and neural cell adhesion molecule (NCAM) in CSF from patients with ALS", Acta Neurol. Scand., 79(3):177-181 (1989).

Wilkinson, J.H., "Synthesis of some Possible Metabolites of Thyroxine and Triiodothyronine", Biochem. J., 63:601-605 (1956) 5 pages.

Xia et al., "Chemokines/chemokine receptors in the central nervous system and Alzheimer's disease", J. NeuroVirol., 5:32-41 (1999) 11 pages.

Yalcin et al., "Tetraidothyroacetic Acid (Tetrac) and Tetrac Nanoparticles Inhibit Growth of Human Renal Cell Carcinoma Xenografts", Anticancer Res., 29:3825-3832 (2009) 7 pages.

Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 7 pages.

Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 9 pages.

(56) References Cited

OTHER PUBLICATIONS

Yalcin et al., "Tetraiodothyroacetic Acid and Tetraiodothyroacetic Acid Nanoparticle Effectively Inhibit the Growth of Human Follicular Thyroid Cell Carcinoma", Thyroid, 20(3):281-286 (2010) 6 pages.
Yanase et al., "Role of N-methyl-D-aspartate receptor in acute spinal cord injury", J. Neurosurg., 83:884-888 (1995) 6 pages.
Yang et al., "Rab7b, a novel lysosome-associated small GTPase, is involved in monocytic differentiation of human acute promyelocytic leukemia cells", Biochem. Biophys. Res. Commun., 318:792-799 (2004) 8 pages.
Yang, et al., "enhanced inhibition of adipogenesis and induction of apoptosis in 3T3-L1 adipocytes with combinations of resveratrol and quercetin", Life Sci., 82:1032-1039 (2008) 8 pages.
Yonkers et al., "Sensory Neuron Sodium Current Requires Nongenomic Actions of Thyroid Hormone During Development", J. Neurophysiol., 100:2719-2725 (2008) 7 pages.
Young, W., "Role of Calcium in Central Nervous System Injuries", J. Neurotrauma, 9(Suppl. 1): S9-S25 (1992) 18 pages.
Young, W., "Secondary injury mechanisms in acute spinal cord injury", J. Emerg. Med., 11:13-22 (1993) 11 pages.
Yu et al., "Osteopontin Gene is Expressed in the Dermal Papilla of Pelage Follicles in a Hair-Cycle-Dependent Manner", J. Invest. Dermatol., 117:1554-1558 (2001) 5 pages.
Yu, et al., "The Compressor Silencing Mediator for Retinoid and Thyroid Hormone Receptor Facilitates Cellular Recovery from DNA Double-Strand Breaks", Cancer Res., 66(18):9316-9322 (2006) 7 pages.
Zhang et al., "Oestrogen inhibits resveratrol-induced post-translational modification of p53 and apoptosis in breast cancer cells", Br. J. Cancer, 91:178-185 (2004) 8 pages.
Zhang et al., "Quantitative PET Imaging of Tumor Integrin $\alpha v \beta 3$ Expression with 18F-FRGD2", J. Nucl. Med., 47:113-121 (2006) 9 pages.
Zhen et al., "Synthesis and Amyloid Binding Properties of Rhenium Compleses: Preliminary Progress Toward a Reagent for SPECT Imaging of Alzheimer's Disease Brain", J. Med. Chem., 42:2805-2815 (1999) 11 pages.
Zhuang et al., "99mTc-Labeled MIBG Derivatives: Novel 99m Tc Complexes as Myocardial Imaging Agents for Sympathetic Neurons", Bioconjugate Chem., 10:159-168 (1999) 10 pages.
Office Action (Mail Date Apr. 11, 2013) for U.S. Appl. No. 12/816,287, filed Jun. 15, 2010.
Office Action (Mail Date Apr. 8, 2013) for U.S. Appl. No. 11/786,723, filed Apr. 11, 2007.
Office Action (Mail Date Apr. 12, 2013) for U.S. Appl. No. 12/751,375, filed Mar. 31, 2010.
De la Cruz et al., "Effect of Aspirin Plus Dipyridamole on the Retinal Vascular Pattern in Experimental Diabetes Mellitus", J. Pharmacol. Exp. Ther., 280(1):454-459 (1997) 6 pages.
Deardorff, D.L., "Isotonic Solutions", in Remington's Pharmaceutical Sciences, 15th Ed., Chapter 79, pp. 1405-1412, Mack Publishing Co., Easton (1975) 10 pages.
DeFesi et al., "3,5,3'-Triiodothyronine Effects on the Growth Rate and Cell Cycle of Cultured GC Cells", Endocrinol., 108(1):259-267(1981) 9 pages.
Demediuk et al., "Traumatic Spinal Cord Injury in Rats Causes Increases in Tissue Thromboxane But Not Peptidoleukotrienes", J. Neurosci. Res., 20:115-121 (1988) 7 pages.
DeRyck et al., "Neocortical localization of tactile/proprioceptive limb placing reactions in the rat", Brain Res., 573 (1):44-60 (1992) 18 pages.
Di Chiro et al., "Glucose utilization of cerebral gliomas measured by [18F] fluorodeoxyglucose and positron emission tomography", Neurology, 32(12):1323-1329 (1982) 8 pages.
Dietrich et al., "Post-traumatic brain hypothermia reduces histopathological damage following concussive brain injury in the rat", Acta Neuropathol., 87(3):250-258 (1994) 10 pages.

Ding et al., "Radioprotection of Hematopoietic Tissue by Fibroblast Growth Factors in Fractionated Radiation Experiments", Acta Onocol., 36(3):337-340 (1997) 4 pages.
Dixon et al., "A fluid percussion model of experimental brain injury in the rat", J. Neurosurg., 67(1):110-119 (1987) 11 pages.
Drusano et al., "Pharmacodynamics of Abacavir in an In Vitro Hollow-Fiber Model System", Antimicrob. Agents Chemother., 46(2):464-470 (2002) 7 pages.
Dupont et al., "Antiangiogenic and antimetastatic properties of Neovastat (•-941), an orally active extract derived from cartilage tissue", Clin. Experim. Metastasis, 19:145-153 (2002) 9 pages.
Edwards et al., "Trypsinized BHK21 cells aggregate in the presence of metabolic inhibitors and in the absence of divalent cations", J. Cell Sci., 19(3):653-667 (1975) 16 pages.
Elkind et al., "Radiation Response of Mammalian Cells Grown in Culture. 1. Repair of X-Ray Damage in Surviving Chinese Hamster Cells", Radiat. Res., 13:556-593 (1960) 38 pages.
Elvin et al., "Cell Adhesiveness and the Cell Cycle: Correlation in Synchronized Balb/c 3T3 Cells", Biol. Cell, 48:1-10 (1983) 10 pages.
Ely and Berne, "Protective Effects of Adenosine in Myocardial Ischemia", Circulation, 85:893-904 (1992) 13 pages.
Ethier et al., "Adenosine stimulates proliferation of human endothelial cells in culture", Am. J. Physiol., 265:H131-H138 (1993) 8 pages.
Everts et al., "Uptake of 3,3',5.5'-Tetraiodothyroacetic Acid and 3,3',5'-Triiodothyronine in Cultured Rat Anterior Pituitary Cells and Their Effects on Thyrotropin Secretion", Endocrinol., 136(10):4454-4461 (1995) 8 pages.
Faden et al., "Endogenous Opioid Immunoreactivity in Rat Spinal Cord Following Traumatic Injury", Ann. Neurol., 17 (4):386-390 (1985) 5 pages.
Faden, A.I., "Experimental Neurobiology of Central Nervous System Trauma", Crit. Rev. Neurobiol., 7(3/4):175-186 (1993) 13 pages.
Feeney et al., "Amphetamine, Haloperidol, and Experience Interact to Affect Rate of Recovery After Motor Cortex Injury", Science, 217(4562):855-857 (1982) 4 pages.
Fei et al., "P53 and radiation responses", Oncogene, 22:5774-5783 (2003) 10 pages.
Felding-Habermann et al., "Integrin activation controls metastasis in human breast cancer", Proc. Natl. Acad. Sci. U.S.A., 98(4):1853-1858 (2001) 6 pages.
Feng et al., "Fibrin and Collagen Differentially Regulate Human Dermal Microfascular Endothelial Cell Integrins: Stablization of $\alpha \square / \beta 3$ mRNA by Fibrin", J. Invest. Dermatol., 113(6):913-919 (1999) 7 pages.
Fife et al., "Effects of tetracyclines on angiogenesis in vitro", Cancer Letters, 153:75-78 (2000) 4 pages.
Folkman, J., "Angiogenesis in cancer, vascular, rheumatoid and other disease", Nat. Med., 1(1):27-31 (1995) 5 pages.
Freese et al., "Characterization and mechanism of glutamate neurotoxicity in primary striatal cultures", Brain Res., 521 (1/2):254-264 (1990) 12 pages.
Frye, R.A., "Characterization of Five Human cDNAs with Homonology to the Yeast SIR2. Gene: Sir2-like Proteins (Sirtuins) Metabolize NAD and May Have Protein ADP-Ribosyltransferase Activity", Biochem. Biophys. Res. Comm., 260:273-279 (1999) 7 pages.
Fujii et al., "Crystal Structure of Trimestatin, a Disintegrin Containing a Cell Adhesion Recognition Motif RGD", J. Mol. Biol., 332:1115-1122 (2003) 8 pages.
Gavrieli et al., "Identification of Programmed Cell Death in Situ via Specific Labeling of Nuclear DNA Fragmentation", J. Cell. Biol., 119(3):493-501 (1992) 9 pages.
GenBank Accession No. AF083106, Apr. 14, 2000 5 pages.
GenBank Accession No. AF083107, Mar. 21, 2001. 3 pages.
GenBank Accession No. NM_002210, Jun. 15, 2008 8 pages.
GenBank Accession No. NM_012238, Apr. 25, 2010. 8 pages.
GenBank Accession No. NM_030593, Mar. 14, 2010. 8 pages.
GenBank Accession No. NP_036370, Apr. 25, 2010. 6 pages.
GenBank Accession No. NP_501912, Nov. 13, 2008. 4 pages.
GenBank Accession No. P53685, Apr. 20, 2010. 8 pages.

(56) References Cited

OTHER PUBLICATIONS

Geng et al., "A Specific Antagonist of the p110σ Catalytic Component of Phosphatidylinositol 3'-Kinase, IC486068, Enchances Radiation-Induced Tumor Vascular Destruction", Cancer Res., 64:4893-4899 (2004) 7 pages.
Ginis et al., "Hypoxia affects tumor cell invasiveness in vitro: the role of hypoxia-activated ligand HAL 1/13 (Ku 86 autoantigen)", Cancer Lett., 154:163-174 (2000) 12 pages.
Gladson, C.L., "Expression of integrin α☐β3 in Small Blood Vessels of Giioblastoma Tumors", J. Neurpath. Exp. Neurol., 55(11):1143-1149(1996) 7 pages.
Glinskii et al., "Modification of survival pathway gene expression in human breast cancer cells by tetraiodothyroacetic acid (tetrac)", Cell Cycle, 8(21):3562-3570 (2009) 9 pages.
Glinsky et al., "Classification of Human Breast Cancer Using Gene Expression Profiling as a Component of the Survival Predictor Algorithm", Clin. Cancer Res., 10:2272-2283 (2004) 12 pages.
Glinsky et al., "Gene expression prfiling predicts clinical outcome of prostate cancer", J. Clin. Invest., 113(6):913-923 (2004) 11 pages.
Glinsky et al., "Microarray analysis identifies a death-from-cancer signature predicting therapy failure in patients with multiple types of cancer", J. Clin. Invest., 115(6):1503-1521 (2005) 19 pages.
Glinsky et al., "Microarray Analysis of Xenograft-Derived Cancer Cells Lines Representing Multiple Experimental Models of Human Prostate Cancer", Mol. Carcinog., 37:209-221 (2003) 13 pages.
Goldstein et al., "Influence of Lesion Size and Location on Amphetamine-Facilitated Recovery of Beam-Walking in Rats", Behav. Neurosci., 104(2):320-327 (1990) 9 pages.
Goldstein, A., "Estimating the Error Variance and the Confidence Interval for a Regression Line", in Biostatistics, The MacMillan Co., New York, pp. 139-146 (1964) 10 pages.
Goodman, M.M., "Automated Synthesis of Radiotracers for PET Applications", in Clinical Positron Emission Tomography, Mosby Yearbook, K.F. Hubner et al., Chapter 14, pp. 110-122 (1992) 13 pages.
Grant, D.B., "Monitoring TSH concentrations during treatment for gongenital hypothyroidism", Arch. Disease Childhood, 66:669-670 (1991) 2 pages.
Gregoriadis, "Liposomes", in Drug Carriers in Biology and Medicine, Chapter 14, pp. 287-341, Academic Press (1979) 57 pages.
A.D.A.M. Medical Encyclopedia, www.ncbi.nlm.nih.gov/pubmedhealth/PMH0001308/, downloaded Jul. 12, 2012. 6 pages.
Abdollahi et al., "Inhibition of α☐β3 Integrin Survival Signaling Enhances Antiangiogenic and Antitumor Effects of Radiotherapy", Clin. Cancer Research., 11(17):6270-6279 (2005) 10 pages.
Albert et al., "Integrin α☐β3 Antagonist Cilengitide Enhances Efficacy of Radiotherapy in Endothelial Cell and Non-Small-Cell Lung Cancer Models", Int. J. Radiat. Oncol. Biol. Phys., 65(5):1536-1543 (2006) 8 pages.
Alexis et al., "Nonocclusive Common Carotid Artery Thrombosis in the Rat Results in Reversible Sensorimotor and Cognitive Behavorial Deficits", Stroke, 26:2338-2346 (1995) 16 pages.
Ali et al., "Angiogenesis as a potential biomarker in prostate cancer chemoprevention trials", Urology, 57(Suppl 4A):143-147 (2001) 5 pages.
Ali et al., "Apoptosis-Inducing effect of erlotinib is potentiated by 3,3'-diindolylmethane in vitro and in vivo using an orthotopic model of pancreatic cancer", Mol. Cancer Ther., 7(6):1708-1719(2008) 12 pages.
Ali et al., "High levels of oestrogen receptor-α in tumorigenesis: inhibition of cell growth and angiogenic factors", Cell Prolif., 34(4):223-231 (2001) 10 pages.
Allen, A.R., "Surgery of experimental lesion of spinal cord equivalent to crush injury of fracture dislocation of spinal column", J. Am. Med. Assoc., 57(11):878-880 (1911) 4 pages.
Almog et al., "Transcriptional Switch of Dormant Tumors to Fast-Growing Angiogenic Phenotype", Cancer Res., 69 (3):836-844 (2009).
Amirkhosravi et al., "Antimestatatic effect of tinzaparin, a low-molecular-weight heparin", J. Thromb. Haemost., 1:1972-1976 (2003) 5 pages.
Amirkhosravi et al., "Inhibition of tumor cell-induced platelet aggregation and lung metastasis by the oral Gpllb/Illa antagonist XV454", J. Thrombosis and Haemostasis, 3:549-554 (2003) 6 pages.
Ando et al., "Induction by carbon-ion irradiation of the expression of vascular endothelial growth factor in lung carcinoma cells", Int. J. Radiat. Biol., 76(8):1121-1127 (2000) 7 pages.
Application No. PCT/US2004/030583, International Search Report and the Written Opinion of the International Searching Authority, or the Declaration dated Mar. 7, 2005. 11 pages.
Application No. PCT/US2005/032813, International Search Report dated Dec. 22, 2006. 6 pages.
Application No. PCT/US2007/009026, International Search Report dated Nov. 7, 2008. 5 pages.
Application No. PCT/US2009/069104, International Search Report dated Mar. 4, 2010 5 pages.
Application No. PCT/US2007/026167, International Search Report dated Oct. 30, 2008. 3 pages.
Application No. PCT/US2010/038700, International Search Report dated Mar. 21, 2011. 4 pages.
Application No. PCT/US2006/036243, International Search Report dated Jul. 30, 2007. 7 pages.
Application No. PCT/US2010/029371, International Search Report dated Aug. 24, 2010. 5 pages.
Audus et al., "Bovine Brain Microvessel Endothelial Cell Monolayers as a Model System for the Blood-Brain Barrier", in Biological Approaches to the Controlled Delivery of Drugs, Ann. N.Y. Acad. Sci., 507:9-18 (1987) 11 pages.
Avis, K.E., "Parenteral Preparations", in Remington's Pharmaceutical Sciences, 15th Ed., Chapter 84, pp. 1461-1487, Mack Publishing Co., Easton, Pennsylvania (1975) 29 pages.
Balestrazzi et al., "Leaf-associated bacteria from transgenic white poplar producing resveratrol-like compounds: isolation, molecular characterization, and evaluation of oxidative stress tolerance", Can. J. Microbiol., 55:829-840 (2009) 12 pages.
Balin-Gauthier et al., "In vivo and in vitro antitumor activity of oxaliplatin in combination with cetuximab in human colorectal tumor cell lines expressing different level of EGFR", Cancer Chemother. Pharmacol., 57:709-718 (2006) 8 pages.
Baur et al., "Resveratrol improves health and survival of mice on a high-calorie diet", Nature, 444:337-342 (2006) 6 pages.
Baur et al., "Therapeutic potential of resveratrol: the in vivo evidence", Nat. Rev. Drug Discov., 5:493-506 (2006) 14 pages.
Bederson et al., "Rat Middle Cerebral Artery Occlusion: Evaluation of the Model and Development of a Neurologic Examination", Stroke, 17(3):472-476 (1986) 6 pages.
Belenky et al., "NAD+ metabolism in health and disease", Trends Biochem. Sci., 32(1):12-19 (2007) 9 pages.
Benedetti et al., "Life Tables and Survivor Functions", in BMDP Statistical Software Manual, BMDP Statistical Software, Inc., vol. 2, p. 573 and 689-718 (1988) 33 pages.
Ben-Hur et al., "Thermally Enhanced Radioresponse of Cultured Chinese Hamster Cells: Inhibition of Repair of Sublethal Damage and Enhancement of Lethal Damage", Radiat Res., 58:38-51 (1974) 14 pages.
Bennett et al., "A peptide derived from α-fetoprotein prevents the growth of estrogen-dependent human breast cancers sensitive and resistant to tamoxifen", Proc. Natl, Acad. Sci. USA, 99(4):2211-2215 (2002) 5 pages.
Li et al., "Requirement of hypoxia-inducible factor-1α down-regulation in mediating the antitumor activity of the anit-epidermal growth factor receptor monoclonal antibody cetuximab", Mol. Cancer Ther., 7(5):1207-1217 (2008) 11 pages.
Lin et al., "Androgen-induced human breast cancer cell proliferation is mediated by discrete mechanisms in estrogen receptor-α-positive and -negative breast cancer cells", J. Steroid Biochem. Mol. Biol., 113:182-188 (2009) 7 pages.

(56) References Cited

OTHER PUBLICATIONS

Lin et al., "Identification of the Putative Map Kinase Docking Site in the Thyroid Hormone Receptor-β1 DNA-Binding Domain: Functional Consequences of Mutations at the Docking Site", Biochem., 42:7571-7579 (2003) 9 pages.
Lin et al., "Integrin α☐β3 contains a receptor site for resveratrol", FASEB J., 20(10): 1742-1744 (2006) 3 pages.
Lin et al., "L-Thyroxine vs. 3,5,3'-triiodo-L-thyronine and cell proliferation: activation of mitogen-activated protein kinase and phosphatidylinositol 3-kinase", Am. J. Physiol. Cell Physiol., 296:C980-C991 (2009) 12 pages.
Lin et al., "Resveratrol Causes COX-2- and p53-Dependent Apoptosis in Head and Neck Squamos Cell Cancer Cells", J. Cell Biochem., 104:2131-2142 (2008) 12 pages.
Lin et al., "Resveratrol Induced Serine Phosphorylation of p53 Causes Apoptosis in a Mutant p53 Prostate Cancer Cell Line", J. Urol., 168:748-755 (2002) 8 pages.
Lin., et al., "Resveratrol is pro-apoptotic and thyroid hormone is anti-apoptotic in glioma cells: both actions are integrin and ERK mediated", Carcinogenesis, 29(1):62-69 (2008) 8 pages.
Lin et al., "The pro-apoptotic action of stilbene-induced COX-2 in cancer cells: Convergence with the anti-apoptotic effect of thyroid hormone", Cell Cycle, 8(12):1877-1882 (2009) 6 pages.
Lin et al., "Thyroid hormone is a MAPK-dependent growth factor for thyroid cancer cells and is anti-apoptotic", Steriods, 72:180-187 (2007) 8 pages.
Liu et al., "Calcineurin Is a Common Target of Cyclophilin-Cyclosporin A and FKBP-FK506 Complexes", Cell, 66:807-815 (1991) 9 pages.
Lorger et al., "Activation of tumor cell integrin α☐β3 controls angiogenesis and metastatic growth in the brain", Proc. Natl. Acad. Sci. U.S.A., 106(26):10666-10671 (2009) 7 pages.
Louie et al., "Pharmacodynamics of Levofloxacin in a Murine Pneumonia Model of Pseudomonas aeruginosa Infection: Determination of Epithelial Lining Fluid Targets", Antimicrob Agents Chemother., 53(8):3325-3330 (2009) 6 pages.
Luidens et al., "Thyroid hormone and angiogenesis", Vascular Pharmacology, 52(3-4):142-145 (2010) 4 pages.
Lyons et al., "The Expression of an N-CAM Serum Fragment is Positively Correlated with Severity of Negative Featues in Type II Schizophrenia", Biol. Psychiatry, 23:769-775 (1988) 7 pages.
Ma, et al., "Use of Encapsulated Single Chain Antibodies for Induction of Anti-Idiotypic Humoral and Cellular Immune Responses", J. Pharm. Sci., 87:1375-1378 (1998). 4 pages.
Mahmood et al., "An N2S2 Teradentate Chelate for Solid-Phase Synthesis: Evaluation in Solution and Solid Phase and Characterization of Technetium-99 Complexes", Technetium, Rhenium and Other Metals in Chemistry and Nuclear Medicine, 5:71-76 (1999) 6 pages.
Mandelin et al., "Extracellular and Intracellular Mechanisms That Mediate the Metastatic Activity of Exogenous Osteopontin", Cancer, 115:1753-1764 (2009) 12 pages.
Mangale et al., "Identification of genes regulated by an interaction between α☐β3 integrin and vitronectin in murine decidua", Reprod. Fertil. Dev., 20:311-319 (2008) 10 pages.
Markgraf et al., "Sensorimotor and cognitive consequences of middle cerebral artery occlusion in rates", Brain Res., 575(2):238-246 (1992) 10 pages.
Martens et al., "Inhibition of Glioblastoma Growth in a Highly Invasive Nude Mouse Model Can Be Achieved by Targeting Epidermal Growth Factor Receptor but not Vascular Endothelial Growth Factor Receptor-2", Clin. Cancer Res., 14(17):5447-5458 (2008) 12 pages.
Masson-Gadais et al., "Integrin α☐β3 requirement for VEGFR2-mediated activation of SAPK2/p38 and Hsp90-dependent phosphorylation of focal adhesion kinase in endothelial cells activated by VEGF", Cell Stress Chaperones, 8(1):37-52 (2003) 16 pages.
McCarty et al., "Promises and Pitfalls of Anti-Angiogenic Therapy in Clinical Trials." Trends Mol. Med. 9.2(2003):53-58 6 pages.
Meneses et al., "Recombinant angiostatin prevents retinal neovascularization in a murine proliferative retinopathy model", Gene Therapy, 8(8):646-648 (2011) 3 pages.
Mezosi et al., "Nongenomic effect of thyroid hormone on free-radical production in human polymorphonuclear leukocytes", J. Endocrinol., 185:121-129 (2005) 9 pages.
Mishkin et al., "Increased Survival of Rats Bearing Morris Hepatoma 7800 after Induction of Hypothroidism", Cancer Res., 39:2371-2375 (1979) 5 pages.
Miyaguchi et al., "Correlation of Epidermal Growth Factor Receptor and Radiosensitivity in Human Maxillary Carcinoma Cell Lines", ActaOtolaryngol., 118:428-431 (1998) 4 pages.
Moeller et al., "Cytosolic Action of Thyroid Hormone Leads to Induction of Hypoxia-inducible Factor-1α and Glycolytic Genes", Molec. Endo., 19(12):2955-2963 (2005) 9 pages.
Moeller et al., "Thyroid hormone mediated changes in gene expression can be initiated by cytosolic action of the thyroid hormone receptor beta through the phosphatidylinositol 3-kinase pathway", Nuclear Receptor Signaling, 4: E020 (2006) 4 pages.
Mohamed et al., "Wound healing properties of cimetidine in vitro", Drug Intell. Clin. Pharm., 20(12):973-975 (1986) 4 pages.
Monferran et al., "α☐β3 and α☐β5 integrins control glioma cell response to ionising radiation through ILK and RhoB", Int. J. Cancer, 123:357-364 (2008) 8 pages.
Morand et al., "Effect of Iodide on Nicotinamide Adenine Dinucleotide Phosphate Oxidase Activity and Duox2 Protein Expression in Isolated Porcine Thyroid Follicles", Endo., 144(4):1241-1248 (2003) 8 pages.
Moreno et al., "Metabolic Effects of Thyroid Hormone Derivatives", Thyroid, 18(2):239-253 (2008) 15 pages.
Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", Thyroid, 18 (2):239-253 (2008) 15 pages.
Mousa et al., "Cellular and Molecular Mechanisms of Nicotine's Pro-Angiogenesis Activity and Its Potential Impact on Cancer", J. Cell. Biochem., 97:1370-1378 (2006) 9 pages.
Mousa et al., "Discovery of Pro-Angiogenic Effects of Nicotine's Pro-Angiogenesis Activity and Its Potential Impact on Cancer", J. Cell. Biochem., 97:1370-1378 (2006) Abstract Only. 3 pages.
Mousa et al., "Proangiogenesis Action of the Thyroid Hormone Analog 3,5-Diiodothyropropionic Acid (DITPA) Is Initiated at the Cell Surface and is Integrin Mediated", Endocrinol., 147(4):1602-1607 (2006) 6 pages.
Mousa et al., "Pro-angiogenesis action of thyroid hormone and analogs in a three-dimensional in vitro microvascular endothelial sprouting model", Int. Angiol., 25(4):407-413 (2006) 7 pages.
Mousa et al., "Tetraiodothyroacetic (tetrac) inhibits angiogenesis, In: Program of the 77th Annual Meeting of the American Thyroid Association", Phoenix, AZ, 2006: Abstract 108. 4 pages.
Mousa et al., "Tetraiodothyroacetic acid, a small molecule integrin ligand, blocks angiogenesis induced by vascular endothelial growth factor and basic fibroblast growth factor", Angiogenesis, 11:183-190 (2008) 8 pages.
Mousa et al., "The Proangiogenic Action of Thyroid Hormone Analogue GC-1 Is Initiated at an Integrin", J. Cardiovasc. Pharmacol., 46(3):356-360 (2005) 6 pages.
Mousa, S.A., "Mechanisms of Angiogenesis: Potential Therapeutic Targets", in Angiogenesis Inhibitors and Stimulators: Potential Therapeutic Implications, Landes Bioscience, Georgetown, Texas, Chapter I, pp. 1-12 (2000) 14 pages.
Mousa, S.A., et al., "Effect of Resveratrol on Angiogenesis and Platelet/Fibrin-Accelerated Tumor Growth in the Chick Chorioallantoic Membrane Model," Nutr. Cancer, 52(1):59-65 (2005) 7 pages.
Muller et al., "The Double Life of the Ku Protein: Facing the DNA Breaks and the Extracellular Environment", Cell Cycle, 4(30:438-441 (2005) 4 pages.
Ndiaye et al., "Red wine polyphenol-induced, endothelium-dependent NO-mediated relaxation is due to the redox-sensitive PI3-kinase / Akt-dependent phosphorylation of endothelial NO-synthase in the isolated porcine coronary artery", FASEB J., 19(3):455-457 (2005) 3 pages.

(56) References Cited

OTHER PUBLICATIONS

Nehls et al., "A microcarrier-based concultivation system for the investigation of factors and cells involved in angiogenesis in three-dimensional fibrin matrices in vitro", Histochem. Cell Biol., 104(6):459-466 (1995) 8 pages.

Nehls et al., "A Novel Micrcarrier-Based in Vitro Assay for Rapid and Reliable Quantification of Three-Domensional Cell Migration and Angiogenesis", Microvasc. Res., 50(3):311-322 (1995) 12 pages.

Neises et al., "Esterification of Carboxylic Acids with Dicyclohexylcarbodiimide/4-Dimethylaminopyridine: tert-Butyl Ethyl Fumarate", Org. Synth., 7:93 (1990); 63:183 (1985) 3 pages.

Office Action (Mail Date Apr. 29, 2013) for U.S. Appl. No. 13/345,194, filed Jan. 6, 2012.

Notice of Allowance (Mail Date Oct. 4, 2013) for U.S. Appl. No. 11/786,723, filed Apr. 11, 2007.

Office Action (Mail Date Oct. 15, 2013) for U.S. Appl. No. 13/345,194, filed Jan. 6, 2012.

Office Action (Mail Date Apr. 2, 2013) for U.S. Appl. No. 13/156,047, filed Jun. 8, 2011.

Office Action (Mail Date Feb. 25, 2014) for U.S. Appl. No. 13/156,047, filed Jun. 8, 2011.

U.S. Appl. No. 14/184,889, filed Feb. 20, 2014.
U.S. Appl. No. 14/185,010, filed Feb. 20, 2014.
U.S. Appl. No. 14/078,713, filed Nov. 13, 2013.
U.S. Appl. No. 13/975,725, filed Aug. 26, 2013.
U.S. Appl. No. 12/751,375, filed Mar. 31, 2010.
U.S. Appl. No. 13/345,194, filed Jan. 6, 2012.
U.S. Appl. No. 13/156,047, filed Jun. 8, 2011.
U.S. Appl. No. 12/644,493, filed Dec. 22, 2009.
U.S. Appl. No. 11/786,723, filed Apr. 11, 2007.
U.S. Appl. No. 12/816,287, filed Jun. 15, 2010.
U.S. Appl. No. 12/947,389, filed Nov. 16, 2010.

Notice of Allowance (Mail Date Feb. 6, 2014) for U.S. Appl. No. 13/345,194, filed Jan. 6, 2012.

Office Action (Mail Date Mar. 12, 2014) for U.S. Appl. No. 12/947,389, filed Nov. 16, 2010.

Office Action (Mail Date May 8, 2014) for U.S. Appl. No. 12/816,287, filed Jun. 15, 2010.

Guigon et al., "Regulation of β-Catenin by a Novel Nongenomic Action of Thyroid Hormone β Receptor", Mol. Cell. Biol., 28(14):4598-4608 (2008) 11 pages.

Hahn et al., "Plateau-phase cultures of mammalian cells: An in vitro model for human cancer", Curr. Top. Radiat. Res. Q., 8:39-83 (1972) 45 pages.

Halks-Miller et al., "CCR1 Immunoreactivity in Alzheimer's Disease Brains", Society for Neuroscience Meeting, Abstract #787.6, vol. 24 (1998) Abstract Only. 1 page.

Hansebout, R.R., "A Comprehensive Review of Methods of Improving Cord Recovery After Acute Spinla Cord Injury", in Early Management of Acute Spinal Cord Injury, pp. 181-196 (1982) 16 pages.

Harter, H., "Blutgerinnungsstud Mit Der Thrombelastogeraphie, Einem Neuen Untersuchungsverfahren", Klinische Wochenschrift 26(37/38):577-583 (1948) German Language Only. 9 pages.

Hashimoto et al., "Matrix Metalloproteinases Cleave Connective Tissue Growth Factor Reactivate Angiogenic Activity of Vascular Endothelial Growth Factor 165", J. Biol. Chem. 277(39):36288-36295 (2002) 8 pages.

Heller et al., "Inhibition of potentially lethal damage recovery by altered pH, glucose utilization and proliferation in plateau growth phase human glioma cells", Int. J. Radiat. Biol., 66(1):41-47 (1994) 7 pages.

Hercbergs et al., "GL261 brain tumor cells: responses to signle or fractionated x-irradiation with the α□β3 integrin tyroxine receptor antagonist tetrac (tetraiodothyroacetic acid)", 20th EORTC-NCI-AACR Symposium on Molecular Targets and Cancer Therapeutics, Geneva, Switzerland, Oct. 2008. 304 pages.

Hercbergs et al., "GL261 brain tumor cells: responses to single or fractionated x-irradiation with the α□β3 integrin tyroxine receptor antagonist tetrac (tetraiodothyroacetic acid)", Euro. J. Cancer, 6(12):172 (Abstract Only) 4 pages.

Hercbergs et al., "Propylthiouracil-induced Chemical Hypothyroidism with High-Dose Tamoxifen Prolongs Survival in Recurrent High Grade Ciioma: A Phase I/II Study", Anticancer Res., 23:617-626 (2003) 10 pages.

Hercbergs, A., "The Thyroid Gland as an Intrinsic Biologic Response-Modifier in Advanced Neoplasia—A Novel Paradigm", in vivo, 10:"245-247 (1996) 3 pages.

Hercbergs, et al., GL261 Brain Tumor Cells: In Vitro Single and Fractionated Dose Responses to X-Rays and Modification by Tetrac (Tetraiodothyroacetic Acid), The Cleveland Clinic Foundation, Department of Radiation Oncology 46 pages.

Hercbergs, et al., "Radiosensitization of GL261 glioma cells by tetraiodothyroacetic acid (tetrac)", Cell Cycle, 8 (16):2586-2591 (2009) 6 pages.

Hermanson, "Modification with Synthetic Polymers", in Bioconjugate Tech., Ch. 15, Academic Press, San Diego, CA, pp. 617-618 (1996) 4 pages.

Hoff et al., "Medullary Thyroid Carcinoma", Hematol. Oncol. Cin. North Am., 21(3):475-488 (2007) 14 pages.

Horuk et al., "Expression of Chemokine Receptors by Subsets of Neurons in the Central Nervous System", J. Immunol., 158:2882-2890 (1997) 9 pages.

Hubner, K.F., "University of Tennessee Biomedical Imaging Center and Transfer of Technology to the Clinical Floor", in Clinical Positron Emission Tomography, Mosby Yearbook, K.F. Hubner et al., Chapter 2, pp. 4-16(1992) 13 pages.

Hudlicka et al., "Factors involved in capillary growth in the heart", Mol. Cell. Biochem, 147:57-68 (1995) 12 pages.

Igarashi et al., "Techniques Supporting Angiogenesis Therapy 2: DDS Technique Supporting Regenerative Medicine." Inflamm. Immun. 10.6(2002):652-658 7 pages.

Illario et al., "Fibronectin-Induced Proliferation in Thyroid Cells is Mediated by α□β3 Integrin through Ras/Raf-1/MEK/ERK and Calcium/CaMKII Signals", J. Clin. Endocrinol. Metab., 90(5):2865-2873 (2005) 9 pages.

Ingerman-Wojenski et al., "Evaluation of electrical aggregometry: comparison with optial aggregometry, secretion of ATP, and accumulation of radiolabeled platelets", J. Lab. Clin. Med., 101(1):44-52 (1983) 10 pages.

Iwata et al., "A new, convenient method for the preparation of 4-[18F]fluorobenzyl halides", Applied Radiation and Isotopes, 52(1):87-92 (2000) 7 pages.

Jain, K.K., "Strategies and technologies for drug delivery systems", TIPS, 19:155-157 (1998) 5 pages.

Janssen et al., "Pathogenesis of Spinal Cord Injury and Newer Treatments—A Review", Spine, 14(1):23-32 (1989) 11 pages.

Jeffrey et al., "The preparation and characterisation of poly(lactide-co-glycolide) microparticles. 1. Oil-in-water emulsion solvent evaporation", Int. J. Pharm., 77:169-175 (1991) 7 pages.

Jonker et al., "Cetuximab for the Treatment of Colorectal Cancer", N. Engl. J. Med., 357(20):2040-2048 (2007) 9 pages.

Jordan et al., "Thyroid Status is a Key Modulator of Tumor Oxygenation: Implication for Radiation Therapy", Radiat. Res., 168:428-432 (2007) 5 pages.

Kalofonos et al., "Monoclonal Antibodies in the Management of Solid Tumors", Curr. Top. Med. Chem., 6:1687-1705 (2006) 19 pages.

Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", Radiat. Res., 113:458-472 (1988) 15 pages.

Kastan et al., "A Mammalian Cell Cycle Checkpoint Pathway Utliziing P53 and GADD45 is Defective in Ataxia-Telangiectasia", Cell. 71:587-597 (1992) 11 pages.

Kawasuji et al., Jap. Circ. J., 63(Suppl. 1):65 (1999) Japanese Abstract Only. 3 pages.

Kerr et al., "Novel Small Molecule α□ Integrin Antagonists: Comparative Anti-Cancer Efficacy with Known Angiogenesis Inhibitors", Anticancer Res., 19:959-968 (1999).

(56) References Cited

OTHER PUBLICATIONS

Kerr et al., "Small molecule α integrin antagonists: novel anticancer agents", Exp. Opin. Invest. Drugs, 9 (6):1271-1279 (2000) 9 pages.
Kim et al., "Regulation of Antiogenesis in Vivo, by Ligation of Integrin α5β1 with the Central Cell-Binding Domaing of Fibronectin", Am. J. Pathol., 156(4): 1345-1362 (2000) 18 pages.
Kim et al., "Soluble Flt-1 gene delivery using PEI-g-PEG-RGD conjugate for anti-angiogenesis", J. Control Release, 106:224-234 (2005) 11 pages.
Kimelberg, H.K., "Astrocytic Edema in CNS Trauma", J. Neurotrauma, 9(Suppl. 1):S71-S81 (1992) 12 pages.
Kitevska et al., "Caspase-2: controversial killer or checkpoint controller?", Apoptosis, 14:829-848(2009) 20 pages.
Kleczkowska et al., "Differntial poly(ADP-ribose) metabolism in repair-proficient and repair-deficient murine lymphoma cells", Mut. Res., 235:93-99 (1990) 7 pages.
Klunk et al., "Development of Small Molecule Probes for the Beta-Amyloid Protein of Alzheimer's Disease", Neurobiol. Aging, 15(6):691-698 (1994) 8 pages.
Kobayashi et al., "Drug Delivery Catheter." Surg. Front. 9.1(2002):55-57 3 pages.
Konno et al., "Antiogenetic therapy for carcinoma", Igaku No Ayumi, 194(10): 824-828 (2000) 5 pages.
Koutras et al., "Antiproliferative effect of exemestane in lung cancer cells", Mol. Cancer, 8(1):109 (2009) 12 pages.
Koyama et al., "Recent Status and Future Perspectives in Therapeutic Angiogenesis", Prog. Med., 22(12):3070-3076 (2002) (English Abstract) 7 pages.
Kramer et al., "Human Microvascular Endothelial Cells Use β1 and β3 Integrin Receptor Complexes to Attach to Laminin", J. Cell Biol., 111:1233-1343 (1990) 11 pages.
Kumar et al., "Enhancing Effect of Thyroxine on Tumor Growth and Metastases in Syngeneic Mouse Tumor Systems", Cancer Res., 39:3515-3518 (1979) 4 pages.
Kuroki et al., "Diabetic retinopathy—The mechanisms of the ocular neovascularization of the development of anti-angiogenic drugs-", Nippon Rinsho, 57(3):584-589 (1999) (English Abstract Only) 6 pages.
Kwok et al., "Differences in EGF rated radiosensitisation of human squamous carcinoma cells with high and low number of EGF receptors", Br. J. Cancer, 64:251-254 (1991) 4 pages.
Lameloise et al., "Differences between the effects of thyroxine and tetraiodothyroacetic acid on TSH suppression and cardiac hypertrophy", Eur. J. Endocrinol., 144:145-154 (2001) 10 pages.
Lawler et al., "Cell Attachment to Thombospondin: The Role of ARG-GLY-ASP, Calcium and Integrn Receptors", J. Cell Biol., 107(6 Pt. 1): 2351-2361 (1988) 11 pages.
Letterio et al., "Maternal Rescue of Transforming Growth Facotr-β1 Null Mice", Science, 264:1936-1938 (1994) 4 pages.
Bergers et al., "Modes of resistance to anti-angiogenic therapy", Nat. Rev. Cancer, 8(8):592-603 (2008) 23 pages.
Bergh et al., "Integrin αβ3 contains a cell surface receptor site for thyroid hormone that is linked to activation of mitogen-activated protein kinase and induction of angiogenesis", Endocrinology, 146(7):2864-2871 (2005) 8 pages.
Bergstrom et al., "Iodine-123 labelled Z-(R,R)-IQNP: a potential radioligand for visualization of M1 and M2 muscarinic acetylcholine receptors in Alzheimer's disease", Eur. J. Nucl. Med., 26(11):1482-1485 (1999).
Bergstrom et al., "Reduction of fibrinogen absorption on PEG-coated polystyrene surfaces", J. Biomed. Mat. Res., 26:779-790 (1992) 12 pages.
Beum et al., "Binding of Rituximab, Trastuzumab, Cetuximab, or mAb T101 to Cancer Cells Promotes Trogocytosis Mediated by THP-1 Cells and Monocytes", J. Immunol., 181:8120-8132 (2008) 13 pages.
Bhat et al., "NCAM-180, the largest component of the neural cell adhesion molecule, is reduced in dysmyelinating quaking mutant mouse brain", Brain Res., 452:373-377 (1988) 5 pages.

Bilello et al., "Effect of 2', 3'-Didehydro-3'-Deoxythymidine in an In Vitro Hollow-Fiber Pharmacodynamic Model System Correlates with Results of Dose-Ranging Clinical Studies", Antimicrob Agents Chemother., 38(6):1386-1391 (1994) 6 pages.
Blaszczyk-Thurin et al., "An Experimental Vaccine Expressing Wild-Type p53 induces Protective Immunity Against Glioblastoma Cells with High Levels of Endogenous p53", Scand. J. Immunol., 56:361-375 (2002) 15 pages.
Blight, A.R., "Macrophages and Inflammatory Damage in Spinal Cord Injury", J. Neurotrauma, 9(Suppl. 1):S83-S91 (1992) 10 pages.
Blood et al., "Tumor interactions with the vasculature: angiogenesis and tumor metastasis", Bioch. Biophys. Acta, 1032:89-118 (1990) 30 pages.
Bokemeyer et al., "Fluorouracil, Leucovorin, and Oxaliplatin With and Without Cetuximab in the First-Line Treatment of Metastatic Colorectal Cancer", J. Clin. Oncol., 27(5):663-671 (2009) 9 pages.
Bornebroek et al., "Potential for imaging cerebral amyloid deposits using 123I-labelled serum amyloid P component and SPET", Cucl. Med. Commun., 17:929-933 (1996) 6 pages.
Bozarth et al., "An improved method for the quantitation of cellular migration: Rose of αβ integrin in endothelial and smooth muscle cell migration", Meth. Cell Sci., 19(3):179-187 (1997) 9 pages.
Brachmann et al., "The SIR2 gene family, conserved from bacteria to humans, functions in silencing, cell cycle progression, and chromosome stability", Genes Dev. 9:2888-2902 (1995) 15 pages.
Braughler et al., "Involvement of Lipid Peroxidation in CNS Injury", J. Neurotrauma, 9(Suppl. 1):S1-S7 (1992) 8 pages.
Breier et al., "The role of vascular endothelial growth factor in blood vessel formation", Trends in Cell Biol., 6:454_456 (1996) 3 pages.
Bridoux et al., "Semisynthesis and pharmacological activities of Tetrac analogs: Angiogenesis modulators", Bioorg. Med. Chem. Lett., 19:3259-3263 (2009) 5 pages.
Bridoux et al., "Semisynthesis and pharmacological activities of thyroxine analogs: Development of new angiogenesis modulators", Bioorg. Med. Chem. Lett, 20(11):3394-3398 (2010) 5 pages.
Brockhoff et al., "Differential impact of Cetuximab, Pertuzumab and Trastuzumab on BT474 and SK-BR-3 breast cancer proliferation", Cell Prolif., 40:488-507 (2007) 20 pages.
Brooks et al., "Antintegrin αβ3 blocks human breast cancer growth and angiogenesis in human skin", J. Clin. Invest., 96(4):1815-1822 (1995) 8 pages.
Bulitta et al., "Development and Qualification of a Pharmacodynamic Model for the Pronounced Inoculum Effect of Ceftazidime against Pseudomonas aeruginosa", Antimicrob. Agents Chemother., 53(1):46-56 (2009) 11 pages.
Burgman et al., "Effect of Inhibitors of Poly(ADP-Ribose)Polymerase on the Radiation Resposne of HeLa S3 Cells", Radiat. Res., 119:380-386 (1989) 7 pages.
Carmeliet et al., "Molecular Basis of Angiogenesis Role of VEGF and VE-Cadherin", Ann. N.Y. Acad. Sci., 902:249-264 (2000) 16 pages.
Chanoine et al., "The role of transthyretin in the transport of thyroid hormone to cerebrospinal fluid and brain", Acta Medica Austriaca, 19(Suppl. 1):25-28 (19920) 5 pages.
Charness et al., "Ethanol Increases the Expression of Functional Delta-Opioid Receptors in Neurblastoma x Glioma NG108-15 Hybrid Cells", J. Biol. Chem., 261(7):3164-3169 (1986) 6 pages.
Charo et al., "The Vitronectin Receptor αβ3 Binds Fibronectin and Acts in Concert with α5 β1 in Promoting Cellular Attachment and Spreading on Fibronectin", J. Cell Biol., 111(6 Pt. 1): 2795-2800 (1990) 6 pages.
Chase et al., "Principles of Radioisotope Methodology", 2nd Ed., Minneapolis, MN. Burgess Publ. Co., 1962, pp. 68, 87-90. 7 pages.
Chavakis et al., "Kinetics of integrin expression in the mouse model of proliferative retinopathy and success of secondary intervention with cyclic RGD peptides", Diabetologia, 45:262-267 (2002) 6 pages.
Cheng et al., "Molecular Aspects of Thyroid Hormone Actions", Endocri. Rev., 31(2): 139-170 (2010) 32 pages.
Cheresh et al., "Biosynthetic and Functional Properties of an Arg-Gly-Asp-directed Receptor Involved in Human Melanoma Cell

(56) References Cited

OTHER PUBLICATIONS

Attachment to Vitronectin, Fibrinogen and von Willibrand Factor", J. Biol. Chem., 262(36):17703-17711 (1987) 9 pages.
Cheresh, D.A., "Human endothelial cells synthesize and express an Arg-Gly-Asp-directed adhesion receptor involved in attachment to fibrinogen and von Willibrand factor", Proc. Natl. Acad. Sci. U.S.A., 84:6471-6475 (1987) 9 pages.
Chiaguri et al., "Anoikis: A necessary death program for anchorage-dependent cells", Biochem. Pharmacol., 76:1352-1364 (2008) 13 pages.
Chinese Office Action for Application No. 2004800331846 dated Mar. 5, 2010 7 pages.
Chinese Office Action for Application No. 2004800331846, mailed Nov. 30, 2007, cited CN 1126589. 6 pages.
Clifton et al., "Marked Protection by Moderate Hypothermia After Experimental Traumatic Brain Injury", J. Cereb. Blood Flow Metab., 11(1):114-121 (1991) 9 pages.
Cody et al., "Molecular modeling of the thyroid hormone interactions with $\alpha\beta3$ integrin", Steriods, 72:165-170 (2007) 6 pages.
Cohen-Jonathan et al., "Radioresistance Induced by the High Molecular Forms of the Basic Fibroblast Growth Factor Is Associated with an increased G2 Delay and a Hyperphosphorylation of p34CDC2 in HeLa Cells", Cancer Res., 57:1364-1370 (1997) 7 pages.
Cohen-Jonathan et al., "$\alpha\beta3$ integrin pathway controls glioma radioresistance through ILK", Proc. Amer. Assoc. Cancer Res., 47:5180 (2006) (Abstract Only) 2 pages.
Cox et al., "The repair of potentially lethal damage in X-irradiated cultures of normal and ataxia telangiectasia human fibroblasts", Int. J. Radiat. Biol., 39(4):357-365 (1981) 9 pages.
Cristofanilli et al., "Thyroid Hormone and Breast Carcinoma. Primary Hypothyroidism is Associated with a Reduced Incidence of Primary Breast Carcinoma", Cancer, 103(6):1122-1128 (2005) 7 pages.
D'Arezzo et al., "Rapid Nongenomic Effects of 3,5,3'-Triiodo-L Thyronine on the Intracellular pH of L-6 Myoblasts are Mediated by Intracellular Calcium Mobilization and Kinase Pathways", Endocrinol., 145(12):5694-5703 (2004) 10 pages.
Database Biosis [Online], Accession No. PREV200400161 59, Abstract, Mousa et al., "Discovery of pro-angiogenic effects of thyroid hormone and analogs", Blood, 102(11):77b-78b (2003) 1 page.
Davis et al., "Acting via a Cell Surface Receptor, Thyroid Hormone is a Growth Factor for Glioma cells," Cancer Res., 66(14):7270-7275 (2006) 6 pages.
Davis et al., "Cell-surface receptor for thyroid hormone and tumor cell proliferation", Expert Reviews in Endicrinology and Metabolism, 1(6):753-761 (2006) 10 pages.
Davis et al., "Mechanisms of nongenomic actions of thyroid hormone", Frontiers Neuroendocrinol., 29:211-218 (2008) 8 pages.
Davis et al., "Proangiogenic Action of Thyroid Hormone is Fibroblast Growth Factor-Dependent and is initiated at the Cell Surface." Cir. Res., 94(2004):1500-1506 7 pages.
Davis et al., "Promotion by thyroid hormone of cytoplasm-to-nucleus shutting of thyroid hormone receptors", Steroids, 73:1013-1017 (2008) 5 pages.
Davis et al., "Thyroxine Promotes Association of Mitogen-activated Protein Kinase and Nuclear Thyroid Hormone Receptor (TR) and Causes Serine Phosphorylation of TR", J. Biol. Chem., 275(48):38032-38039 (2000) 8 pages.
Davis et al., "Translational implications of nongenomic actions of thyroid hormone initiated at its integrin receptor", Am. J. Physiol. Endocrinol. Metab., 297:E1238-E1246 (2009) 9 pages.
Newcomb et al., "Radiation Sensitivity of GL261 Murine Glioma Model and Enhanced Radiation Response by Flavopiridol", Cell Cycle, 5(1):93-99 (2006) 7 pages.
Nickoloff et al., "Aberrant Production of Interleukin-8 and Thrombospondin-1 by Psoriatic Keratinocytes Mediates Angiogenesis." Am. J. Pathol. 144.4(1994):820-828 9 pages.
Nilsson et al., "Evidence for Multiple Thyroxine-binding Sites in Human Prealbumin", J. Biol. Chem., 246(19): 6098-6105 (1971) 8 pages.
Ning et al., "Anti-integrin monoclonal antibody CNTO 95 enhances the therapeutic efficacy of fractionated radiation therapy in vivo", Mol. Cancer Ther., 7(6):1569-1578 (2008) 10 pages.
Oak et al., "Antiangiogenic properties of natural polyphenols from red wine and green tea", J. Nutr. Biochem., 16:1-8 (2005) 8 pages.
Okada et al., "A Quantitative in vivo Method of Analyzing Human Tumor-induced Angiogenesis in Mice Using Agarose Microencapsulation and Hemoglobin Enzyme-linked Immunosorbent Assay", Jpn. J. Cancer Res., 86(12):1182-1188 (1995) 7 pages.
Pages et al., "Signaling Angiogenesis via p42/p44 Map Kinase Cascade", Ann. N.Y. Acad., Sci., 902:187-200 (2000) 14 pages.
Painter et al., "Membrane initiation of DNA synthesis", Nature, 270:543 (1977) 1 page.
Panter et al., "Pretreatment with NMDA antagonists limits release of excitatory amino acids following traumatic brain injury", Neurosci. Lett., 136(2):165-168 (1992) 4 pages.
Panyam, et al., "Biodegradable nanoparticles for drug and gene delivery to cells and tissues", Advanced Drug Delivery Reviews, 55: 329-347 (2009) 19 pages.
Pardridge, W.M., "Receptor-Mediated Peptide Transport through the Blood-Brain Barrier", Endocrine Rev., 7 (3):314-330 (1986) 18 pages.
Park et al., "Effects of Tetramethoxystilbene on Hormone-Resistant Breast Cancer Cells: Biological and Biochemical Mechanisms of Action", Cancer Res., 67:5717-5726 (2007) 10 pages.
Parveen, et al., "Polymeric nanoparticles for cancer therapy", Journal of Drug Targeting, 16(2): 108-123, Feb. 2008. 16 pages.
Patel, D.K., "Clinical Use of Anti-Epidermal Growth Factor Receptor Monoclonal Antibodies in Metastatic Colorectal Cancer", Pharacotherapy, 28(11 Pt.2):31S-41S (2008) 12 pages.
Penno et al., "Rapid and quantitative in vitro measurement of cellular chemotaxis and invasion", Meth. Cell Sci., 19:189-195 (1997) 7 pages.
Pirola, et al., "Resveratrol: One Molecule, Many Targets", IUBMB Life, vol. 60, Issue 5, pp. 323-332. 10 pages.
Plow et al., "Ligand Binding to Integrins", J. Biol. Chem., 275(29):21785-21788 (2000) 4 pages.
Powell, J., "The Serial Analysis of Gene Expression", in Meth. Mol. Biol., Chapter 20, 99:297-319 (2000) 23 pages.
Prichard et al., "Concurrent Cetuximab and Bevacizumab Therapy in a Murine Orthotopic Model of Anaplastic Thyroid Carcinoma", Laryngoscope, 117:674-679 (2007) 7 pages.
Pujol et al., "Letter to the editors: Preventioon of thyroid neoplasm recurrence with Triac and levothyroxine", Clin. Endocrinol., 46(1):121-122 (1997) 2 pages.
Raue et al., "Multiple Endocrine Neoplasia Type 2", Horm. Res., 68(Suppl.5): 101-104 (2007) 4 pages.
Rayalam et al., "Resveratrol induces apoptosis and inhibits adipogenesis in 3T3-L1 adipocytes", Phytother. Res., 22:1367-1371 (2008) 5 pages.
Rebbaa et al., "Novel function of the thyroid hormone analog tetraiodothyroacetic acide: a cancer chemosensitizing and anti-cancer agent", Angiogenesis, 11(3):269-276 (2008) 8 pages.
Reinholt et al., "Osteopontin—a possible anchor of osteoclasts to bone", Proc. Natl. Acad. Sci. U.S.A., 87:4473-4475 (1990) 3 pages.
Remsen et al., "Antibodies to the Neural Cell Adhesion Molecule Disrupt Functional Recovery in Injured Nerves", Exp. Neurol., 110:268-273 (1990) 6 pages.
Ren et al., "Regulation of tumor angiogenesis by thrombospondin-1", Biochim. Biophys. Acta. 1765: 178-188 (2006) 11 pages.
Risau, W., "Mechanisims of angiogenesis", Nature, 386:671-674 (1997) 4 pages.
Sahni et al., "Stimulation of endothelial cell proliferation by FGF-2 in the presence of fibrinogen requires $\alpha\beta3$", Blood, 104(12):3635-3641 (2004) 7 pages.
Saito et al., "Vector-mediated delivery of 125I-labeled β-amyloid peptide Aβ1-40 through the blood-brain barrier and binding to Alzheimer disease of the Aβ1-40/vector complex", Proc. Natl. Acad. Sci. US, 92:10227-10231 (1995) 5 pages.

(56) References Cited

OTHER PUBLICATIONS

Samuels et al., "Depletion of L-3-5-3'-Triiodothyronine and L-Thyroxine in Euthyroid Calf Serum for Use in Cell Culture Studies of the Action of Thyroid Hormone", Endo., 105(1):80-85 (1979) 6 pages.
SAS/STAT Guide for Personal Computers, Version 6 Edition, p. 717 (1987) 3 pages.
Sato et al., "Neovascularization: General Remarks", Biotherapy, 15(6):631-636 (2001) (English Abstract) 6 pages.
Scanlan et al., "3-Iodothyronamine is an endogenous and rapid-acting derivative of thyroid hormone", Nat. Med., 10 (6):638-642 (2004) 5 pages.
Scanlan et al., "Selective thyrmimetics: Tissue-selective thyroid hormone analogs", Curr. Opin. Drug Discov. Dev., 4 (5):614-622 (2001) 9 pages.
Schlange et al., "Autocrine WNT signaling contributes to breast cancer cell proliferation via the canonical WNT pathway and EGFR transactivation", Breast Cancer Res., 9:R63 (2007) 15 pages.
Schlumberger et al., "New therapeutic approaches to treat meduliary thyroid carcinoma", Nat. Clin. Prac. Endocrinol. Metab., 4(10):22-32 (2008) 11 pages.
Schnell et al., "Expression of alpha v beta 3 integrin in patients with high and low grade glioma", Proc. Amer. Assoc. Cancer Res., 47:226 (2006) Abstract Only. 5 pages.
Schnell et al., "Expression of Integrin α□β3 in Gliomas Correlates with Tumor Grade and Is not Restricted to Tumor Vasculature", Brain Pathol., 18:378-386 (2008) 9 pages.
Schreiber et al., "Hormone delivery systems to the brain-transhyretin", Exp. Clin. Endocrinol Diabetes, 103(2): 75-80 (1995) 7 pages.
Schueneman et al., "SU11248 Maintenance Therapy Prevents Tumor Regrowth after Fractionated Irradiation of Murine Tumor Models", Cancer Res., 63:4009-4016 (2003) 8 pages.
Shih et al., "Thyroid Hormone Promotes Serine Phosphorylation of p53 by Mitogen-Activated Protein Kinase", Biochem., 40:2870-2878 (2001) 10 pages.
Shih et al., "Disparate Effects of Thyroid Hormone on Actions of Epidermal Growth Factor and Transforming Growth Factor-α Are Mediated by 3,5'-Cyclic Adenosine 5'-Monophosphate-Dependent Protein Kinase II", Endo., 145(4): 1708-1717 (2004) 10 pages.
Shih et al., "Inhibitory effect of epidermal growth factor on resveratrol-induced apoptosis in prostate cancer cells is mediated by protein kinase C-α", Mol. Cancer Ther., 3:1355-1363 (2004) 9 pages.
Shinohara et al., "Enhanced radiation damage of tumor vasculature by mTOR inhibitors", Oncogene, 24:5414-5422 (2005) 9 pages.
Skrovronsky et al., "In vivo detection of amyloid plaques in a mouse model of Alzheimer's disease", Proc. Natl. Acad. Sci US, 97(13):7609-7614 (2000) 6 pages.
Skuli et al., "α□β3/α□β5 integrins-FAK-RhoB: A Novel Pathway for Hypoxia Regulation in Glioblastoma", Cancer Res., 69*8):3308-3316 (2009) 9 pages.
Song et al., "Formulation and characterization of biodegradable nanoparticles for intravascular local drug delivery", J. Controlled Rel., 43:197-212 (1997) 16 pages.
Stefani et al., "The Effect of Resveratrol on a Cell Model of Human Aging", Ann. NY Acad. Sci., 1114:407-418 (2007) 12 pages.
Strieth, et al., "Antiangiogenic combination tumor therapy blocking α□-integrins and VEGF-receptor-2 increases therapeutic effects in vivo", Int. J. Cancer, 119:423-431 (2006) 9 pages.
Sumi et al., "Wound healing using regenerative medicine", Surg. Front., 10(2):162-165 (2003) 4 pages.
Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially p. 230-231.

Avgoustakis, et al., "PLGA-mPEG nanoparticles of cisplatin: in vitro nanoparticle degradation, in vitro drug release and in vivo drug residence in blood properties" J. Contr. Rel. 2002, 79, 123-135. 13 pages.
NCI Cancer Drug Information, Cetuximab, 2006,http://www.cancergovicancertopics/druginfo/cetuxinnab,downloaded Jul. 18, 2014.
Gu et al. 2007, Nanotoday 2:14-21.
Office Action (Mail Date June. 21, 2011) for U.S. Appl. No. 12/947,389, filed Nov. 16, 2010.
Office Action (Mail Date Apr. 4, 2012) for U.S. Appl. No. 12/947,389, filed Nov. 16, 2010.
Office Action (Mail Date Oct. 17, 2012) for U.S. Appl. No. 12/947,389, filed Nov. 16, 2010.
Office Action (Mail Date Apr. 4, 2014) for U.S. Appl. No. 12/947,389, filed Nov. 16, 2010.
Office Action (Mail Date Sep. 4, 2014) for U.S. Appl. No. 12/947,389, filed Nov. 16, 2010.
Office Action (Mail Date May 23, 2012) for U.S. Appl. No. 12/816,287, filed Jun. 15, 2010.
Office Action (Mail Date Oct. 24, 2013) for U.S. Appl. No. 12/816,287, filed Jun. 15, 2010.
Notice of Allowance (Mail Date May 12, 2015) for U.S. Appl. No. 12/816,287.
Office Action (Mail Date May 12, 2015) for U.S. Appl. No. 14/078,713, filed Nov. 13, 2013.
Office Action (Mail Date Mar. 24, 2015) for U.S. Appl. No. 13/975,725, filed Aug. 26, 2013.
Office Action (Mail Date Oct. 5, 2012) for U.S. Appl. No. 12/644,493, filed Dec. 22, 2009.
Office Action (Mail Date Oct. 16, 2014) for U.S. Appl. No. 12/644,493, filed Dec. 22, 2009.
Office Action (Mail Date Apr. 16, 2015) for U.S. Appl. No. 13/156,047, filed Jun. 8, 2011.
Office Action (Mail Date Jul. 13, 2012) for U.S. Appl. No. 12/751,375, filed Mar. 31, 2010.
Office Action (Mail Date Apr. 16, 2015) for U.S. Appl. No. 12/751,375, filed Mar. 31, 2010.
Office Action (Mail Date Jan. 12, 2015) for U.S. Appl. No. 12/751,375, filed Mar. 31, 2010.
Office Action (Mail Date Jun. 3, 2015) for U.S. Appl. No. 12/751,375, filed Mar. 31, 2010.
Application No. PCT/US2010/038700, Supplemental European Search Report dated Apr. 20, 2015. 7 pages.
European Office Action for EP Application No. 07867073.4, mailed on Jul. 16, 2015.
Notice of Allowance (Mail Date Jul. 7, 2015) for U.S. Appl. No. 12/751,375—filed Mar. 31, 2010.
Notice of Allowance (Mail Date Aug. 3, 2015) for U.S. Appl. No. 14/078,713, filed Nov. 13, 2013.
Office Action (Mail Date Mar. 24, 2016) for U.S. Appl. No. 14/546,440, filed Nov. 18, 2014.
Notice of Allowance (Mail Date Nov. 16, 2015) for U.S. Appl. No. 12/947,389, filed Nov. 16, 2010.
Restriction Requirement (Mail Date Dec. 2, 2015) for U.S. Appl. No. 14/184,889, filed Feb. 20, 2014.
Restriction Requirement (Mail Date Dec. 2, 2015) for U.S. Appl. No. 14/185,010, filed Feb. 20, 2014.
Final Office Action (Mail Date Oct. 9, 2015) for U.S. Appl. No. 13/975,725, filed Aug. 26, 2013.
Advisory Action (Mail Date Dec. 31, 2015) for U.S. Appl. No. 13/975,725, filed Aug. 26, 2013.
Notice of Allowance (Mail Date Nov. 2, 2015) for U.S. Appl. No. 13/256,047, filed Jun. 8, 2011.
Restriction Requirement (Mail Date Nov. 4, 2015) for U.S. Appl. No. 14/546,440, filed Nov. 18, 2014.
Restriction Requirement (Mail Date: May 5, 2016) for U.S. Appl. No. 14/977,776.

* cited by examiner

METHOD AND COMPOSITION OF THYROID HORMONE ANALOGUES AND NANOFORMULATIONS THEREOF FOR TREATING ANTI-INFLAMMATORY DISORDERS

RELATED APPLICATIONS

This application claims the benefit of U.S. Application No. 61/807,123, filed Apr. 1, 2013, the content of which is incorporated herein by reference.

FIELD OF TECHNOLOGY

The following relates to polymer conjugate forms of thyroid hormone analogues and derivatives thereof. More specifically the following disclosure relates to embodiments of nanoparticulate tri-iodothyroacetic or tetra-iodothyroacetic acid, alone or in combination with a second agent, such as non-steroidal anti-inflammatory drugs, salicylates, anti-inflammatory glucocorticoids, polyphenols, for management of inflammatory conditions. The disclosure also relates generally to methods of using said embodiments including embodiments to decrease or control inflammation responses by the subject.

BACKGROUND

Thyroid hormones, such as L-thyroxine (T4) and 3, 5, 3'-triiodo-L-thyronine (T3), and their analogues such as GC-1, DITPA, tetraiodothyroacetic acid (tetrac) and triiodothyroacetic acid (triac), regulate many different physiological processes in different tissues in vertebrates. It was previously known that many of the actions of thyroid hormones are mediated by the thyroid hormone receptor ("TR") and a novel cell surface receptor for thyroid hormone (L-thyroxine, T4; T3) integrin $\alpha v\beta 3$, at or near the Arg-Gly-Asp (RGD) recognition site on the integrin. The integrin receptor is not a homologue of the nuclear thyroid hormone receptor (TR), but activation of this cell surface receptor results in a number of nucleus-mediated events. A detailed description of the thyroid hormones, analogs thereof and their properties have been fully discussed and disclosed in US Patent Publication No. 2011/0052715A1 to Davis et al., U.S. Pat. No. 7,785,632 to Mousa et al., and U.S. Pat. No. 8,668,926 to Mousa et al., incorporated by reference in their entirety herein.

Evidence that thyroid hormone can act primarily outside the cell nucleus has come from studies of mitochondrial responses to T3 and diiodothyronine (T2), from rapid onset effects of the hormone at the cell membrane, and from actions on cytoplasmic proteins. The recent description of a plasma membrane receptor for thyroid hormone on integrin $\alpha v\beta 3$ has provided some insight into effects of the hormone on membrane ion pumps, such as the Na+/H+ anti porter, and has led to the description of interfaces between actions initiated at the membrane thyroid hormone receptor and nuclear events that underlie important cellular or tissue processes, such as, for example, angiogenesis and proliferation of certain tumor cells.

Inflammation is closely linked to cancer. Chronic inflammation increases the risk for various cancers, indicating that eliminating inflammation may represent a valid strategy for cancer prevention and therapy. There is data suggesting that inflammation plays a role in the establishment, progression, and/or aggressiveness of various malignancies. As a tumor develops, it expresses phenotypes similar to inflammatory cells. Molecular mediators and their respective receptors have a significant impact on angiogenesis, cell migration, and metastasis. Given its myriad pro-tumor effects, inflammation has become a target for cancer prevention and therapy. COX-2 (cyclooxygenase 2, PTGS2) is the most frequently evaluated anti-cancer anti-inflammatory target, although numerous other targets, such as NF-kB, cytokines/cytokine receptors, chemokines/chemokine receptors, FGF/FGFR (fibroblast growth factor/receptor), and VEGF have also been examined. While initial studies focused on various broad-spectrum NSAIDs (which non-specifically inhibit both COX-1 and COX-2), more recent studies have examined COX-2 specific agents, such as celecoxib. However, given the GI toxicity and non-specific activity of NSAIDs, and the cardio-toxicity of specific COX-2 inhibitors, the use of such agents remains controversial. Therefore, a need exists for the combined use of an effective anti-cancer agent, anti-angiogenic agent and an anti-inflammatory agent capable of being selectively targeted to the tumor cells and reduces inflammation while reducing the toxicity caused by unselective anti-inflammatory agents.

SUMMARY

A first embodiment of this disclosure relates generally to a composition comprising a thyroid hormone antagonist conjugated to a polymer and at least one anti-inflammatory agent encapsulated within the polymer, wherein said at least one anti-inflammatory agent is selected from a non-steroidal anti-inflammatory drug (NSAID), a salicylate, an anti-inflammatory glucocorticoid, and pirfenidone.

A second embodiment of this disclosure relates generally to a method for treating an inflammatory or musculoskeletal condition comprising the steps of conjugating thyroid hormone analogue to a polymer, forming a conjugated thyroid hormone analog, encapsulating inside the polymer of the conjugated thyroid hormone analogue at least one of a non-steroidal anti-inflammatory drug (NSAID), a salicylate, an anti-inflammatory glucocorticoid, and pirfenidone and binding the conjugated thyroid hormone analogue to at least one chemokine receptor, cytokine receptor, interleukin or a combination of receptors thereof.

DETAILED DESCRIPTION OF THE INVENTION

Figure 1:
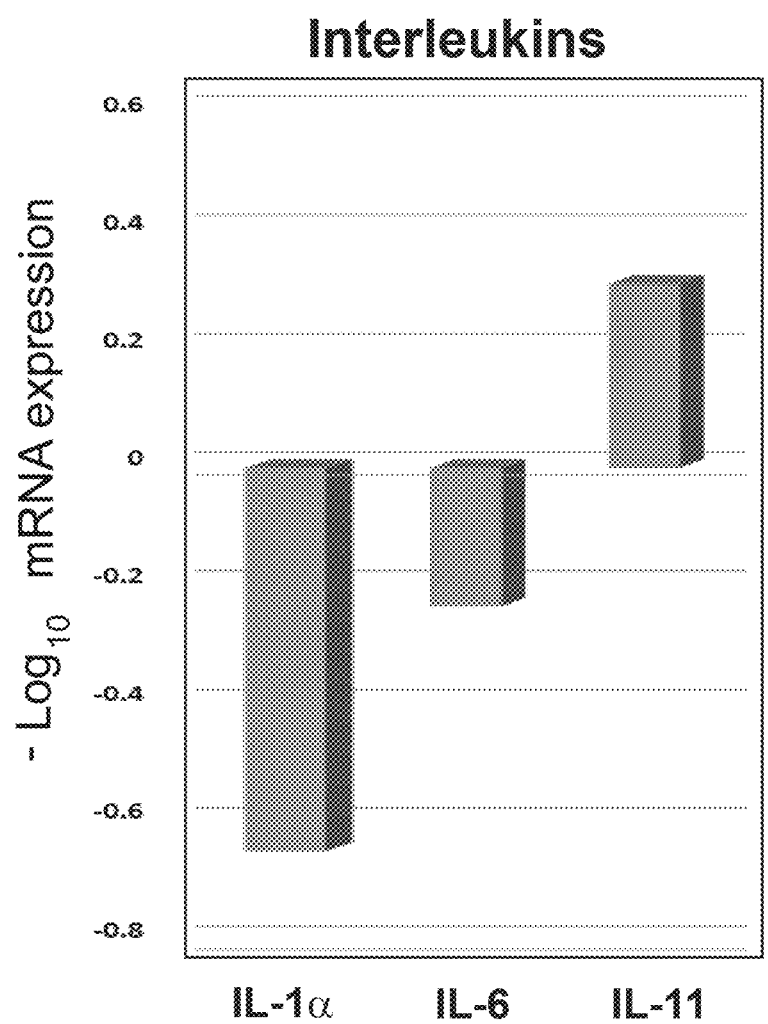
FIG. 1 depicts a graphical representation of the effects of nanoparticulate tetrac treatment on the differentially regulated interleukin genes of human breast cancer MDA-MB-231 cells.

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

Embodiments of the novel compound of this present disclosure may be formulated using a thyroid hormone analogue as a targeting agent and/or inflammation suppressing agent. The targeting agent may direct the novel compound toward the tumor site and/or the site of inflammation. Examples of thyroid hormone analogues are also provided herein and can include triiodothyronine (T3), levothyroxine (T4), T4 or T3 N-Methyl, T4 or T3 N-Ethyl, T4 or T3 N-Triphenyl, T4 or T3 N-Propyl, T4 or T3 N-Isopropyl, T4 or T3 N-tertiary butyl, 3,5-dimethyl-4-(4'-hydroy-3'-isopropylbenzyl)-phenoxy acetic acid (GC-1), or 3,5-diiodothyropropionic acid (DITPA), tetraiodothyroacetic acid (TETRAC), and triiodothyroacetic acid (TRIAC), additional antagonists described below and in Table 1 and pharmaceutically acceptable salts thereof.

"Pharmaceutically acceptable salts" may refer to pharmaceutically acceptable salts of thyroid hormone analogues, polymeric forms, and derivatives, which salts are derived from a variety of organic and inorganic counter ions well known in the art and include, by way of example only, sodium, potassium, calcium, magnesium, ammonium, tetraalkyl ammonium, and the like; and when the molecule contains a basic functionality, salts of organic or inorganic acids, such as hydrochloride, hydro-bromide, tartrate, mesylate, acetate, maleate, oxalate and the like can be used as the pharmaceutically acceptable salt. The term also includes both acid and base addition salts.

The compounds described herein, or their pharmaceutically acceptable salts, may have asymmetric carbon atoms in their structure. The compounds disclosed herein and their pharmaceutically acceptable salts may therefore exist as single enantiomers, diastereoisomers, racemates, and mixtures of enantiomers and diastereomers. All such single enantiomers, diastereoisomers, racemates and mixtures thereof are intended to be within the scope of this invention. Absolute configuration of certain carbon atoms within the compounds, if known, may be indicated by the appropriate absolute descriptor R or S.

In some embodiments, the thyroid hormone analogue may be an anti-angiogenic thyroid hormone analogue, also referred to as a thyroid hormone antagonist. A thyroid hormone analogue may include substances that block L-T3 or L-T4 at the integrin alpha v beta 3 receptors ($\alpha v \beta 3$). The terms "anti-angiogenesis" or "anti-angiogenic" may refer to any compound or substance that inhibits or antagonizes angiogenesis, whether alone or in combination with another substance. Examples of thyroid hormone antagonists may include, but are not limited to, tetraiodothyroacetic acid (tetrac), triiodothyroacetic acid (triac), phthalates, desethylamiodarone, NH-3, sulfonyl nitrophenyl thiazides, DHPPA, and the additional examples shown in Table 1 below.

TABLE 1

THYROID ANTAGONISTS EXAMPLES

| | | |
|---|---|---|
| A. | 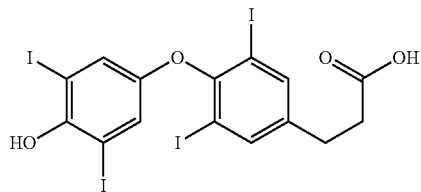 [SMILES: O=C(O)CCc1cc(I)c(Oc2cc(I)c(O)c(I)c2)c(I)c1] | Tetrac |
| B. | 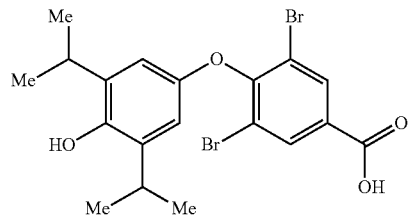 [SMILES: CC(C)c1cc(Oc2c(Br)cc(C(=O)O)cc2Br)cc(C(C)C)c1O] | DIBRT |
| C. | 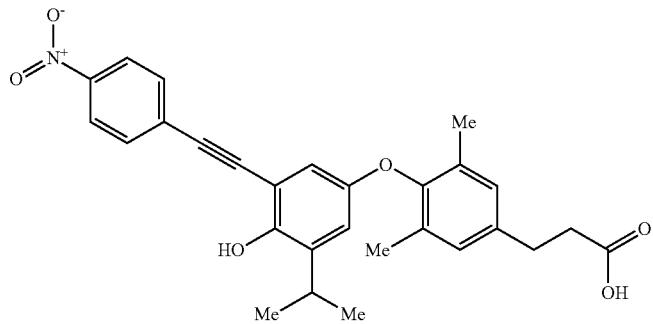 [SMILES: Cc1cc(CCC(=O)O)cc(C)c1Oc1cc(C#Cc2ccc([N+](=O)[O-])cc2)c(O)c(C(C)C)c1] | NH-3 |

TABLE 1-continued
THYROID ANTAGONISTS EXAMPLES
D.
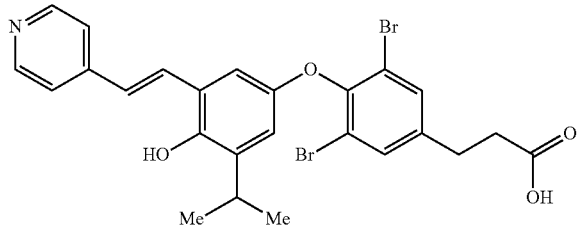 [SMILES: CC(C)c1cc(Oc2c(Br)cc(CCC(=O)O)cc2Br)cc(/C=C/c2ccncc2)c1O]
E.
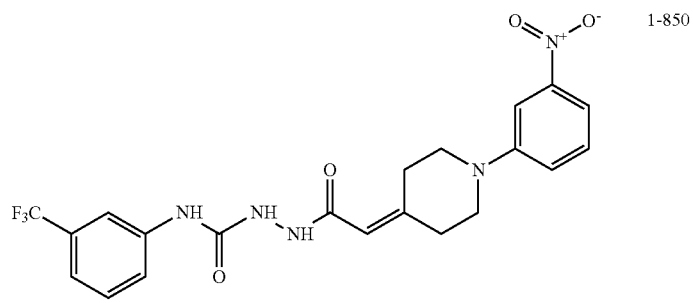
1-850
F.
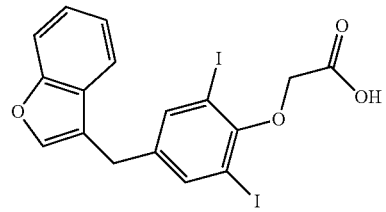 [SMILES: O=C(O)COc1c(I)cc(Cc2coc3ccccc23)cc1I]
G.
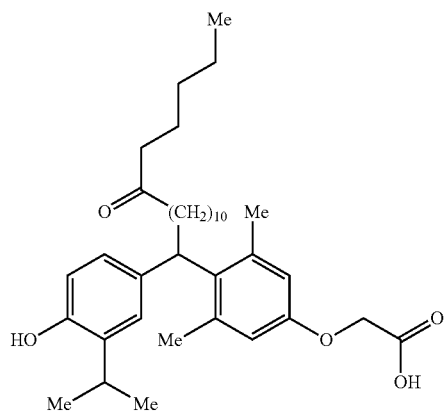
H.
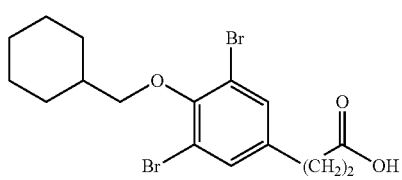

In some embodiments, the thyroid hormone analogue may be conjugated to a polymer. The conjugation between the polymer and the thyroid hormone analogue may occur via a covalent or non-covalent bond, depending on the polymer being used. In some embodiments, the polymer conjugation may occur through an ester linkage, anhydride linkage, ether linkage or sulfhydryl linkage immobilizing the thyroid hormone analogue to the surface of the polymer. In some embodiments, the linkage may include a linker between 3 and 15 atoms long. In alternative embodiments, the linker may be between 3-4, 3-5, 3-6, 3-7 or 3-8 atoms long. The linker between the thyroid hormone analogue and the polymer may be attached on the outer ring hydroxyl group of the thyroid hormone analog. The thyroid hormone analogue conjugated to a polymer described above may be also referred to as a "conjugated thyroid hormone analog."

EXAMPLE 1

Thyroid Hormone Conjugated to a Polymer Via an Ester Linkage

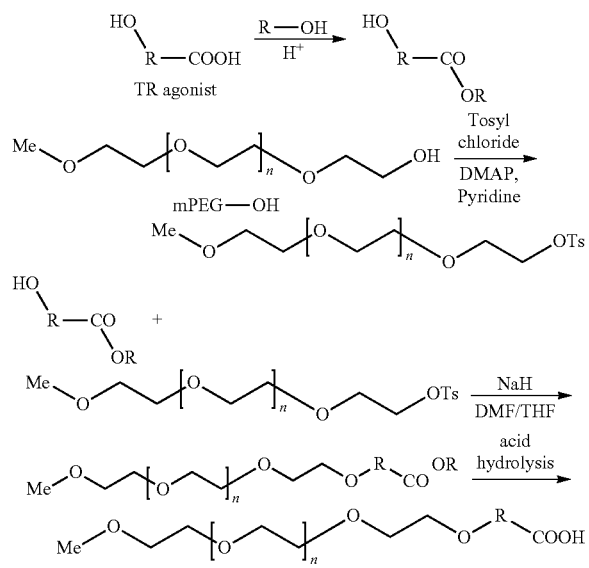

The polymer conjugations may be used to improve drug viability. While many old and new therapeutics are well-tolerated, many compounds may need advanced drug technologies to decrease toxicity, increase circulatory time, or modify biodistribution. One strategy for improving drug viability is the utilization of water-soluble polymers. Various water-soluble polymers have been shown to modify biodistribution, improve the mode of cellular uptake, change the permeability through physiological barriers, and modify the rate of clearance through the body. To achieve either a targeting or sustained-release effect, water-soluble polymers have been synthesized that contain drug moieties as terminal groups, as part of the backbone, or as pendent groups on the polymer chain as well as encapsulating additional compounds inside the polymer to control distribution thereof.

In some embodiments, the polymer that may be conjugated to the thyroid hormone analogue may include but is not limited to polylactic acid (PLLA), polyglycolic acid (PGA), poly(lactic-co-glycolic acid) (PLGA), polyacrylic acid, polyethylene glycol (PEG), poly-L-lysine, chitosan, hyaluronic acid, fatty acids, polyamine, polyvinyl alcohol, acrylic acid ethylene co-polymer, methoxy polyethylene, human serum albumin, polyethylene oxide (PEO), cellulose derivatives, folate linked cyclodextrin, folate linked cyclodextran, alginate, carrageenan, pectin, dextran, collagen, polyaniline, polyalanine, polytryptophan, polytyrosine, co-polymers and combinations thereof.

For example, in one embodiment, a polymer conjugation may be formed through an ester linkage using polyvinyl alcohol. In this preparation commercially available polyvinyl alcohol (or related co-polymers) may be esterified by treatment with the acid chloride of thyroid hormone analogues, including the acid chloride form. The hydrochloride salt may be neutralized by the addition of triethylamine to form triethylamine hydrochloride which can be washed away with water upon precipitation of the thyroid hormone ester polymer form for different analogues.

In an alternative example, a polymer conjugation through an anhydride linkage using acrylic acid ethylene co-polymer similar to the previous polymer covalent conjugation may be used, however, an anhydride linkage that is derived from reaction of an acrylic acid co-polymer may be formed. This anhydride linkage may be susceptible to hydrolysis in vivo to release the thyroid hormone analog. Neutralization of the hydrochloric acid may be accomplished by treatment with triethylamine and subsequent washing of the precipitated polyanhydride polymer with water which removes the triethylamine hydrochloride byproduct. This reaction may lead to the formation of thyroid hormone analogue acrylic acid co-polymer+triethylamine. Upon in vivo hydrolysis, the thyroid hormone analogue may be released over a time frame that can be controlled and manipulated.

In an alternative embodiment, the polymer may be conjugated to the carboxylic acid or the hydroxyl group of the thyroid hormone analogue as depicted in example 2 and example 3 below.

EXAMPLE 2

Route of Tetrac/Polymer Conjugates Synthesis Via Carboxylic Acid Group

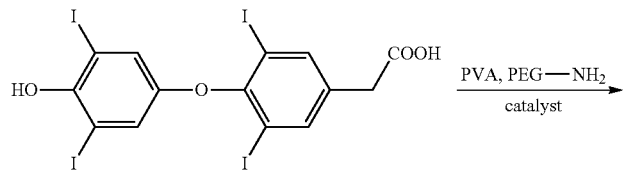

-continued

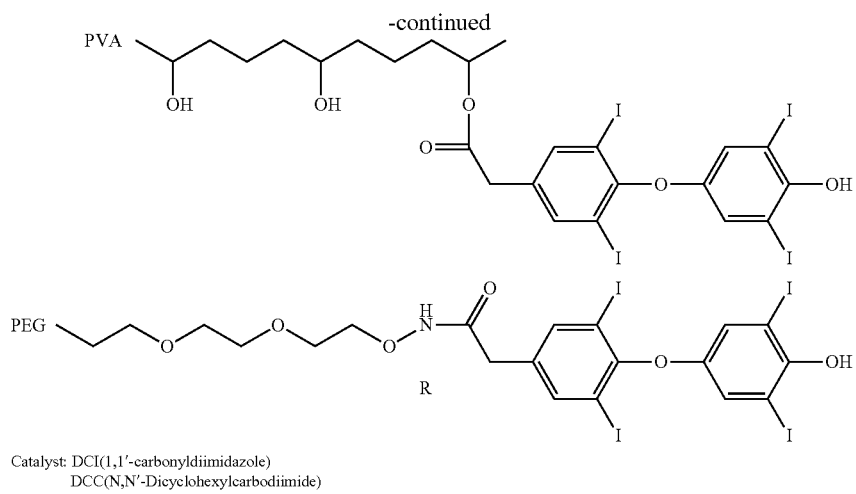

Catalyst: DCI(1,1'-carbonyldiimidazole)
DCC(N,N'-Dicyclohexylcarbodiimide)

EXAMPLE 3

Route of Tetrac/Polymer Conjugates Synthesis Via Hydroxyl Group

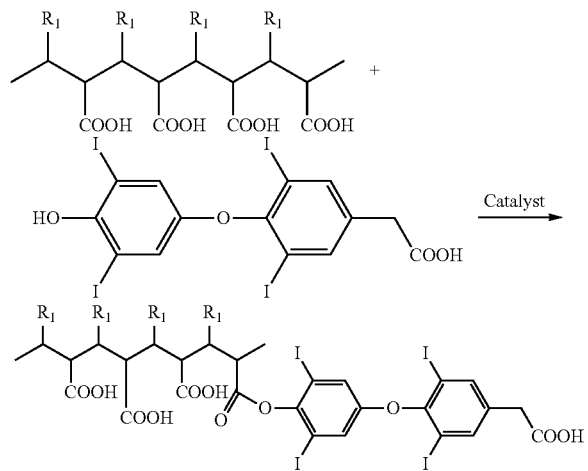

$R_1$ = H poly(acrylic acid)
Me poly(methacrylic acid)
Catalyst: DCI(1,1'-carbonyldiimidazole)
DCC(N,N'-Dicyclohexylcarbodiimide)

In alternative embodiments, a variety of synthetic, natural and biopolymeric side groups with efficient biodegradable backbone polymers may be conjugated to the thyroid hormone analogues. These alternative polymers may include Poly alkyl glycols, polyesters, poly anhydride, poly saccharide, and poly amino acids. Example may include bi-functional PEG, methoxy-PEG, polylactic-co-lysine and polyamidoamine.

Furthermore, in some embodiments, the polymer may be formulated into a microparticle or nanoparticle. As used herein, the term "nanoparticle" refers to particles between about 1 nm and less than 1000 nm in diameter. In suitable embodiments, the diameter of the nanoparticles of the present invention may have a particle size having a diameter between approximately 10 nm to <1000 nm. In other embodiments, the particle may be less than 500 nm in diameter, or less than about 250 nm in diameter. In certain such embodiments, the nanoparticles of the present disclosure may be between about 10 nm and about 200 nm, between about 30 nm and about 100 nm, or between about 40 nm and about 80 nm in diameter. As used herein.

Certain cytokines may cause or be involved in the process of inflammation. For example the pro-angiogenic interleukin-1 (IL-1) may be partially responsible for endogenous inflammatory cytokine release. Anti-angiogenic compounds such as tetrac and triac may be capable of inhibiting pro-angiogenic various cytokines or chemokines. As a result, cytokines or chemokines-mediated angiogenesis contribute to the development of inflammation. The novel compound's inclusion of anti-angiogenic thyroid hormone analogues such as tetrac, triac and nano-formulations thereof may assist in the suppression of cytokines and chemokines responsible for early stage inflammation which may precede an adaptive immune response by the body.

Interleukin responses to conjugated thyroid hormone analog, specifically conjugated nanoparticulate tetrac (Nanotetrac™) were observed in human breast cancer (MDA-MB-231) cells. Referring to the results depicted in FIG. 1, exposure of MDA-MB-231 cells to the Nanotetrac™ acting exclusively at integrin αvβ3, demonstrated a reduction in IL-1α and IL-1β mRNA accumulation by 50-60%. Moreover, it was also determined that the Nanotetrac™ may also reduce interleukin-6 (IL-6) mRNA by 25%, and actually increased interleukin-11 (IL-11) mRNA abundance by 30%. These results demonstrate a selective effect for reduction of the pro-inflammatory IL-1 and IL-6 while also increasing IL-11 which is not pro-inflammatory, but rather a desirable stimulator of hematopoietic stem cell proliferation.

Figure 2:
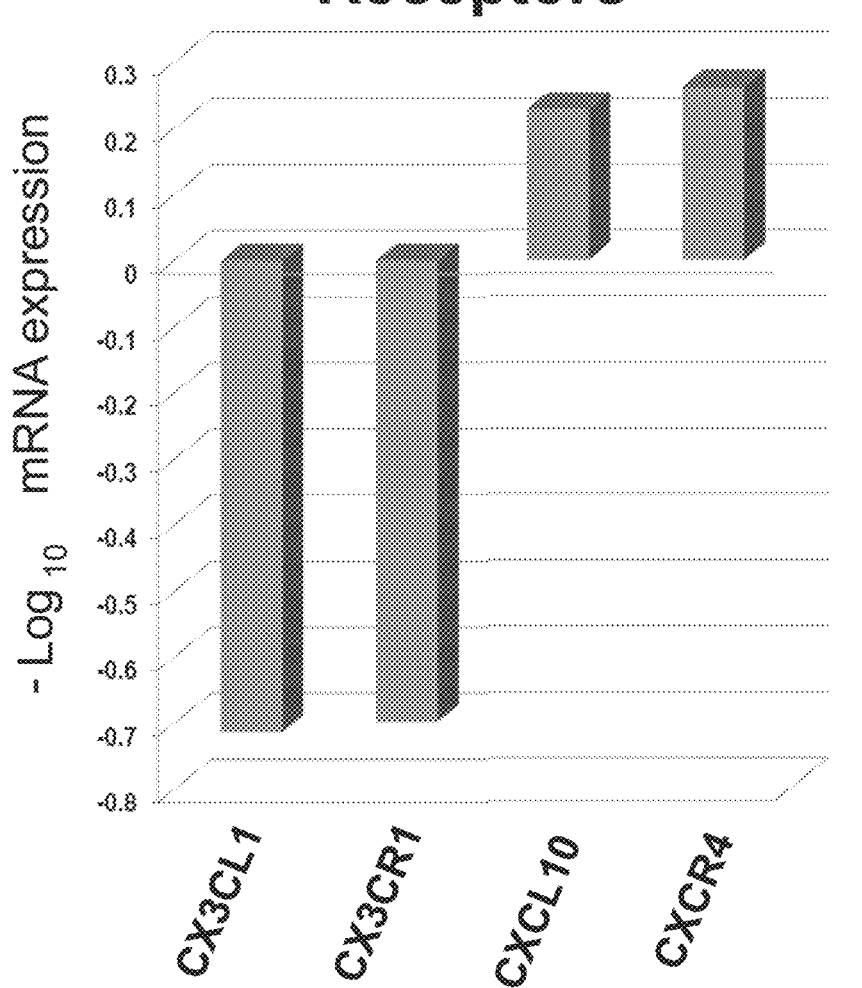
FIG. 2 depicts a graphical representation of the effects of nanoparticulate tetrac on the expression of a plurality of chemokine ligands and receptors in MDA-MBA-231 cells.

Embodiments of the conjugated thyroid hormone analog, such as Nanotetrac™ may also express selective anti-inflammatory effects toward chemokine receptors and chemokine ligand gene expression. For example, studies were performed measuring the effects of Nanotetrac™ on tumor cell expression of the mRNA of the chemokine ligand CX3CL1 (also known as "fractalkine") and the mRNA of its CX3CR1 receptor for fractalkine. Referring to FIG. 2, the results demonstrate that both the expression of CX3CR1 receptor and its CX3CL1 ligand are concomitantly decreased by approximately 75% in response to Nanotetrac™. Fractalkine may mediate chemotaxis and adhesion of inflammatory cells via its receptor. Furthermore, fractalkine may be considered a pharmacologically high priority anti-inflammatory target, because fractalkine may participate in the early inflammatory components of several neurodegenerative diseases, including Alzheimer's disease, Parkinson's disease and HIV-associated encephalopathy.

Still referring to FIG. 2, the results of experimentation further indicate that the chemokine ligand CXCL10 and chemokine receptor CXCR4 may be modestly increased by approximately 20% when cells are exposed to the conjugated thyroid hormone analogue formulation. CXCL10 may be involved in the promotion of apoptosis and of angiostasis. The selective induction of CXC10 may be desirable, and in certain settings the chemokine ligand and receptor can support cell growth and chemotaxis. It is clear based on these findings, that the thyroid hormone receptor on $\alpha v \beta 3$ may selectively mediate thyroid hormone analogue actions on chemokines and their receptors, and that the pharmaceutical targeting of certain chemokine systems may be feasible via $\alpha v \beta 3$ and agents such as Nanotetrac™.

The inhibition of the early inflammatory response (innate immune response) with conjugated thyroid hormone analogue formulations such as Nanotetrac™ may begin at $\alpha v \beta 3$. There are certain actions of agonist thyroid hormones such as T4 and T3 that are relevant to the development and promotion of inflammation, which may be inhibited by conjugated thyroid hormone analogues such as Nanotetrac™. For example, T4 and T3 may act to modulate the production of Signal transducer and activator of transcription-3 (STAT3) which transduces signals of a number of inflammatory cytokines, such as interleukins, and the phosphorylation of STAT3. The regulation of STAT3 may occur by the introduction of pro-angiogenic thyroid hormone, for example the introduction of a pro-angiogenic thyroid hormone concentration such as T4 between $10^{-10}$ to $10^{-7}$ M. The effect of T4 on STAT3 has been reproduced by T4 chemically bonded to agarose (agarose-T4) ($10^{-10}$ M free T4). The binding of T4 to agarose prevents the T4 from gaining access to the cell's interior. The modulation of STAT3 while being unable to enter the cell's interior indicates that the plasma membrane hormone receptor for thyroid hormone on $\alpha v \beta 3$ is involved. Conversely, STAT3's inflammatory response may be reduced or minimized by the introduction of an anti-angiogenic thyroid hormone.

Thyroid hormones may also potentiate certain effects of interferon-γ (IFN-γ) which may also induce certain chemokines as well as refine growth factor signaling at the epidermal growth factor (EGF) receptor (EGFR). It has been determined experimentally that there may be cross-communication between EGFR, cytokine and chemokine signaling pathways that may be stimulated by agarose-T4. The stimulation of these pathways may further implicate $\alpha v \beta 3$ in the IFN-γ and EGFR, as well as STAT3, behaviors described above and the promotion of the inflammatory response. Nanotetrac™ and other conjugated thyroid hormone analogues may inhibit the expression of the EGFR gene, thus reducing the cross communication between EGFR, cytokines and chemokine signal pathways ultimately reducing the overall inflammatory response produced by endogenous thyroid hormone.

As used herein, the phrase "growth factors" or "neurogenesis factors" may refer to proteins, peptides or other molecules having a growth, proliferative, or trophic effect on cells of the CNS or PNS. Such factors may be used for inducing proliferation or differentiation and can include, for example, any trophic factor that allows cells of the CNS or PNS to proliferate, including any molecule which binds to a receptor on the surface of the cell to exert a trophic or growth-inducing effect on the cell. Preferred factors include, but are not limited to, nerve growth factor ("NGF"), epidermal growth factor ("EGF"), platelet-derived growth factor ("PDGF"), insulin-like growth factor ("IGF"), acidic fibroblast growth factor ("aFGF" or "FGF-1"), basic fibroblast growth factor ("bFGF" or "FGF-2"), and transforming growth factor-alpha and -beta ("TGF-α" and "TGF-β").

The integrin $\alpha v \beta 3$ may be generously or overly expressed by tumor cells and dividing blood vessel cells. As disclosed above, thyroid hormones such as tetrac and triac may bind exclusively to the $\alpha v \beta 3$ integrin receptor, making the thyroid hormone of the conjugated thyroid hormone analogue a selective targeting mechanism for tumor cells which express the integrin receptor. Furthermore, conjugated thyroid hormone analogues or other ligands of $\alpha v \beta 3$ may have significant potential either alone or in combination with other anti-inflammatory agents because integrin $\alpha v \beta 3$ is present on plasma membranes of the cells relevant to the formation of inflammation. For example, integrin $\alpha v \beta 3$ may be found on the plasma membrane of neutrophils, peripheral blood lymphocytes, and alveolar macrophages at the sites of lung inflammation.

The early inflammatory component of the innate immune response may include contributions from inflammatory cells, response-modifying cytokines and chemokines and blood vessel growth factors. With regard to the latter, it was pointed out above that Nanotetrac™ may block contributions to the pro-angiogenic component of inflammation via actions on interleukins as well as by decreasing the expression of cytokine and chemokine mRNA. Vascular endothelial growth factor (VEGF), basic fibroblast growth factor (bFGF), platelet-derived growth factor (PDGF), insulin-like growth factor-1 (IGF-1) and EGF are factors that have all been implicated in the vascular phase of the inflammatory response. Acting via the receptor on integrin $\alpha v \beta 3$, Nanotetrac™ and other conjugated thyroid hormone analogues may block the pro-angiogenic actions of each of these factors.

Iodothyronines may also modify activities of inflammatory cells which have been shown to express the thyroid hormone/tetrac receptor-bearing integrin $\alpha v \beta 3$. Acting via the cell surface receptor, thyroid hormone may increase reactive oxygen species ('respiratory burst') in granulocytes. Macrophage function may also be enhanced by thyroid hormone. The latter effect has been thought to result from actions of thyroid hormone within the cell (genomic actions'), but it is clear that thyroid hormone analogues, such as Nanotetrac, act at $\alpha v \beta 3$ to modulate function of nuclear thyroid hormone receptors via control from the integrin of functions of nuclear co-activator proteins and of phosphorylation of nuclear receptor proteins.

Experimental data also suggests that the conjugated thyroid hormone analogues such as Nanotetrac™ formulations may further interfere with gene expression programs triggered in target cells by the increased expression of small non-coding trans-regulatory snpRNAs which are associated with innate immunity/inflammation pathway activation in human cells. Activation of trans-regulatory non-coding snpRNA-associated pathways has been linked with the engagement of the long-range intergenic enhancers and may be pathogenically associated with increased risk of developing prostate cancer and other common human disorders.

Furthermore, in some instances, there is crosstalk between the tetrac-thyroid hormone receptor on integrin $\alpha v \beta 3$ and estrogen receptor-α (ERα) in human lung carcinoma cells that express this estrogen receptor. The proliferative effect of thyroid hormone at $\alpha v \beta 3$ in such cells may be dependent upon ERα. This observation raises the possibility that the actions of thyroid hormone and anti-angiogenic agents on inflammation that are mediated by their receptor on integrin αvβ3 may be involved with other non-peptide hormone response systems that may be regulated at the cell surface.

In one or more embodiments, the conjugated thyroid hormone analogue may further include one or more anti-inflammatory agents encapsulated by the polymer. The anti-inflammatory encapsulated within the polymer may be referred to as the "payload". The amount of the payload the polymer may encapsulate vary depending on the polymer being used and the anti-inflammatory agent being encapsulated. An anti-inflammatory agent may be any substance that has a mechanism of action that reduces, partially reduces or suppresses inflammation. "Encapsulation" may refer to one or more substances surrounding, encasing or protecting another substance, from the environment. For example, in some embodiments, the polymer may shield or protect an anti-inflammatory from harmful conditions in the body that may prematurely break down or degrade the anti-inflammatory agent prior to reaching the target site. In some instances, the anti-inflammatory agent may be encased or fully surrounded by the polymer. In other embodiments, the anti-inflammatory may be bound, attached, adsorbed, or bound to the polymer shielding it using intermolecular forces such as dipole-dipole interactions, ion-dipole interaction, ion-induced interaction, hydrogen bonding, London-dispersion forces, Van der Waals forces, Keesom forces, or Debye forces.

Polymeric microparticles and nanoparticles in some embodiments may be formulated by self-assembly of homopolymers or copolymers. The polymeric particle may include in some embodiments, alternating copolymers or block copolymers consisting of two or more polymer chains with differing hydrophobicity. For instance, in some embodiments, the polymers or copolymers may spontaneously assemble into a core-shell structure in an aqueous environment to minimize the system's free energy. In an instance where a block co-polymer is used, the hydrophobic blocks may form the core to minimize exposure of the aqueous surroundings, whereas a hydrophilic block may form a shell to stabilize the core through direct contact with water.

There are several methods available for preparing polymer microparticles and nanoparticles followed by encapsulating one or more agents, such as anti-inflammatory agents. Methods for preparing the polymeric particles may include emulsification-solvent preparation methods, including single emulsion and double emulsion methods. Some embodiments may use methods such as nano-precipitation (also known as the solvent displacement method), the salting out method or by using microfluidic devices. The choice of the method for preparing the polymeric particle or nanoparticle for encapsulation may vary depending on the nature of the substance being encapsulated or entrapped within the polymeric particle. For the encapsulation of a hydrophilic substance, double emulsion methods may be preferred, whereas for the encapsulation of a hydrophobic substance, nano-precipitation, single emulsion or salting out methods may be used. In some embodiments, the microfluidic device for the formation of polymeric particles may be implemented such as a situation wherein the conditions necessitate fast mixing in homogenous conditions on the micro scale. The release rates of drugs encapsulated inside can be controlled by modifying the polymer's chemical and physical properties.

Figure 3:
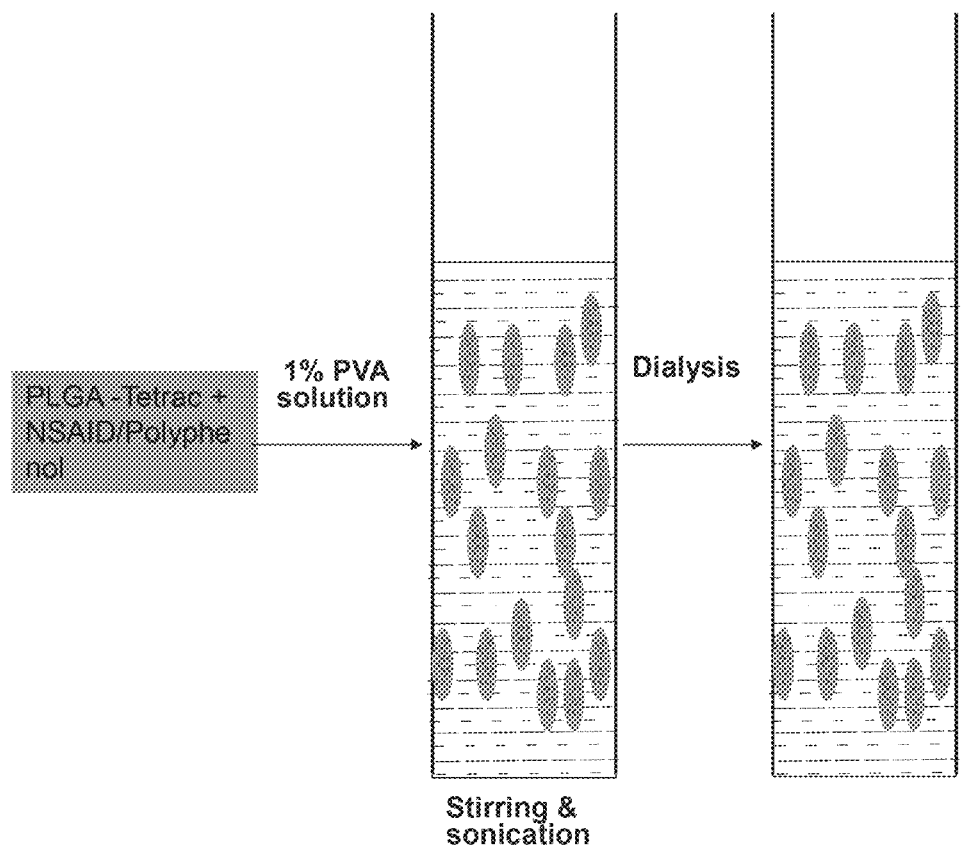
FIG. 3 depicts a representation of the synthesis of thyroid hormone conjugated to a polymer encapsulating an NSAID and/or polyphenol.

For example, in one embodiment, tetrac PLGA nanoparticles encapsulating an NSAID and polyphenols were prepared using a double emulsion and solvent evaporation method. A stock solution of PLGA-Tetrac nanoparticles polymer was prepared by dispersing 100 mg/mL containing 4-8% of Tetrac/PLGA (w/w) in dichloromethane. A stock solution of 10 mg/mL of NSAID and/or polyphenol was prepared by dissolving the NSAID such as ibuprofen and/or polyphenol such as resveratrol in dichloromethane. Five hundred µL of each stock solution was mixed together by vortexing. Then, 1 mL of this solution was mixed with 200 µL of PBS by intermittent sonication (2-3 times, 30 sec each time) to obtain a primary emulsion. As depicted in FIG. 3, the primary emulsion was then intermittently emulsified by sonication (30 s) in 2 mL of 1% w/v PVA solution. This water-in-oil-in-water emulsion was then added to 40 mL of 1.0% PVA solution and stirred for 30 min under constant magnetic stirring. Immediately after, dichloromethane was evaporated at low pressure at 37° C. using a rotatory evaporator. The whole solution was then dialyzed using 10-12 KD dialysis membrane against water for 24 hours to remove the impurities and residual solvents. The entire solution was lyophilized and re-dispersed for further use.

Figure 4:
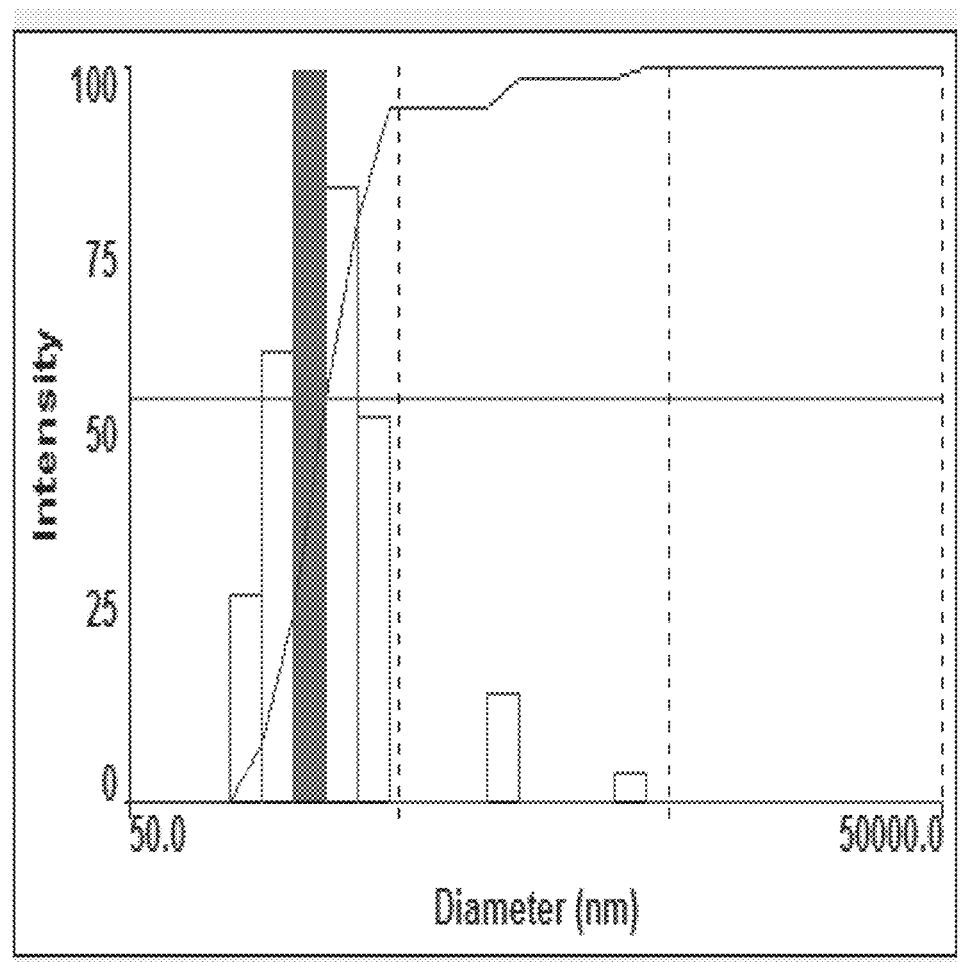
FIG. 4 depicts a graphical representation of the size distribution of tetrac conjugated PLGA nanoparticles encapsulating a polyphenol, resveratrol.

The size distribution of the of the PLGA-tetrac nanoparticles encapsulating resveratrol in an aqueous dispersion using the double emulsion and solvent evaporation method described above, was analyzed by dynamic light scattering (DLS) using a Malvern zeta sizer. After the re-dispersion of the lyophilized powder in deionized water, 1 mL of the NP solution was taken in 3 mL of a four size clear plastic cuvette and measured directly by the DLS. Referring to the results depicted in FIG. 4, the average size of PLGA-Tetrac NPs encapsulating resveratrol ranged from 150-250 nm.

The conjugated thyroid hormone analogue may deliver the anti-inflammatory agent locally to the site of inflammation as the thyroid hormone portion of the conjugated thyroid hormone analogue targets the integrin receptor αvβ3. For example, a tetrac moiety covalently bound to a PLGA polymer may be used as a ligand of αvβ3, expressed by rapidly dividing endothelial cells at the sites of inflammation. The anti-inflammatory agent may be encapsulated by the PLGA particle, thus as the tetrac selectively targets and seeks out the αvβ3 bearing endothelial cells, the PLGA nanoparticle may release the anti-inflammatory agent locally right at the point of inflammation.

The encapsulated anti-inflammatory agents within the polymer may be selected from non-steroidal anti-inflammatory drugs (NSAIDS), salicylates, anti-inflammatory glucocorticoids, anti-fibrotic agents that exhibit anti-inflammatory properties such as pirfenidone, CD-47 antibodies or a combination of anti-inflammatory agents thereof. An NSAID may be any group of anti-inflammatory and analgesic drugs that may suppress inflammation and pain by inhibiting the cyclooxygenase pathway and preventing release of inflammatory mediators (e.g. prostacyclin, prostaglandins and thromboxane). NSAIDs may bind to cyclooxygenase-1 (COX-1), cyclooxygenase-2 (COX-2) or a combination of COX inhibitors. In some embodiments, the NSAIDS encapsulated within the polymer of the conjugated thyroid hormone analogue may include but is not limited to ibuprofen, diclofenac, and diclofenac with misprostol, indomethacin, ketoprofen, fenbrufen, naproxen, sulindac, celecoxib, nabumetone, mefenamic acid, oxyphenbutazone, diflunisal, etodolac, fenoprofen, flurbiprofen, meclofenamate, meloxicam, nabumetone, oxaprozin, piroxicam, tolmetin, valdecoxib and propionic acid derivatives.

In another embodiment, the anti-inflammatory agent may include one or more salicylates encapsulated by the polymer of the conjugated thyroid hormone analogue. A salicylate may be a salt or ester of salicylic acid (C₆H₄(OH)COOH). Salicylates may have an OH group in the ortho position to the carboxyl group. In some instances, a salicylate may be referred to as 2-hydroxybenzoic acid. Similar to the NSAIDs, the salicylates may reduce the onset and extent of inflammation by inhibiting the cyclooxygenase enzyme (COX) production, including both COX-1 and COX-2. Salicylates may include one or more of the following compounds encapsulated inside the polymer of the conjugated thyroid hormone analog, including but not limited to aspirin, choline salicylate, choline and magnesium salicylate, magnesium salicylate, and sodium salicylate.

Embodiments of the conjugated thyroid hormone analogue comprising one or more anti-inflammatory glucocorticoids may include one or more of the following compounds encapsulated by the polymer of the conjugated thyroid hormone analogue. A glucocorticoid may be any corticoid substance that increases gluconeogenesis and may raise the concentration of glycogen in the liver and blood glucose. An anti-inflammatory glucocorticoid may be any glucocorticoid that has an effect on the inflammation response by the body, for example by inhibiting the release of histamine. The glucocorticoids may bind to glucocorticoid receptors in the cytoplasm which then dimerize and translocate to the nucleus, where they bind to glucocorticoid response elements (GRE) on glucocorticoid-responsive genes, resulting in increased transcription. Glucocorticoids may increase the transcription of genes coding for anti-inflammatory proteins, including lipocortin-1, interleukin-10, interleukin-1 receptor antagonist and neutral endopeptidases. The anti-inflammatory response may be due to a direct inhibitory interaction between activated glucocorticoid receptors and activated transcription factors, such as nuclear factor-kappa B and activator protein-1, which regulate the inflammatory gene expression. The glucocorticoids may also inhibit the expression of multiple inflammatory genes such as cytokines, enzymes, receptors and adhesion molecules. Glucocorticoid receptors may also interact with CREB-binding protein (CBP), which may act as a co-activator of transcription, binding several other transcription factors that compete for binding sites on this molecule. Increased transcription may be associated with uncoiling of DNA wound around histone and this may be secondary to acetylation of the histone residues by the enzymatic action of CBP. Glucocorticoids may lead to deacetylation of histone, resulting in tighter coiling of DNA and reduced access of transcription factors to their binding sites, thereby suppressing gene expressions that may lead to inflammation. Said anti-inflammatory glucocorticoids may include, but are not limited to hydrocortisone, cortisone, cortisol, dexamethasone, dexamethasone Intensol™, budesonide, methylprednisolone, prednisolone, prednisolone sodium phosphate and prednisone.

In some embodiments, the anti-inflammatory agent being encapsulated by the polymer may include anti-fibrotic agents having anti-inflammatory properties. An anti-fibrotic agent may be an agent that causes the regression of fibrosis. An example of an anti-fibrotic agent with anti-inflammatory effects may include pirfenidone, NOS-2, daidzein, sirolimus and tyrosine kinase inhibitors including nintendanib.

Embodiments of the anti-inflammatory agent being encapsulated by the polymer may include anti CD47 antibodies. An anti-CD47 antibody may be an anti-body such as a monoclonal or polyclonal antibody that binds to an integrin associated transmembrane protein encoded by the CD47 gene. By inhibiting the CD47 gene with an anti-CD47 antibody, may reduce inflammation by reducing the recruitment of T-cells by the body as well as neutrophils and monocytes at the area of inflammation. Examples of anti-CD47 antibodies may include B6H12.2 (ab3283), EPR4150 (ab108415), ab175388, OX-101 (33852), MEM-122 (ab9089), ab136550, Allophycocyanin (ab134485), ab118222, ab171767, ab176099, ab174029 and human CD47 protein fragment ab151372.

In some embodiments, the polymer of the conjugated thyroid hormone analogue may further include encapsulated anti-oxidant polyphenols inside the polymer for local release at the site of inflammation. A polyphenol may refer to a compound containing one or more phenolic hydroxyl groups. An anti-oxidant polyphenol may be a polyphenol that prevents or inhibits oxidation or reactions promoted by oxidants, such as oxygen, peroxide or free radicals. The anti-oxidant polyphenol may include one or more flavones, isoflavones and/or flavonoids such as resveratrol, quercetin, myricetin, catechin, epigallocatechin, enistein and combinations thereof.

In yet another embodiment, the polymer may encapsulate one or more additional agents to release at thyroid hormone analogue target binding site integrin $\alpha v\beta 3$. One or more additional agents that may be encapsulated within the polymer may include, but is not limited to, bisphosphonates such as risendronate, alendronate, ibandronate, etidronate, pamidronate, tiludronate, and zoledronic acid, growth factors, hormones, enzymes, antibiotics, vasodilators, anti-coagulants, anti-virals, anti-bacterials, immuno-suppressants, analgesics, vascularizing agents, or cell adhesion molecules, or combinations thereof or other bioactive agents.

In some embodiments, the conjugated thyroid hormone analogue, including one or more additionally encapsulated agents may be administered systemically to one or more areas of inflammation or reactive angiogenesis, wherein the integrin receptor may be expressed. The conjugated thyroid hormone analogue, including one or more encapsulated agents, may be administered at a therapeutic concentration of approximately 200-2000 μg/day. In another embodiment, the concentration may vary between 200-1800 μg/day, 300-1700 μg/day, 500-1500 μg/day, 700-1200 μg/day or 800-1000 μg/day.

Nanoparticles within the present disclosure may include up to approximately 100, up to 90, up to 80, up to 70, up to 60, up to 50, up to 40 up to 30, up to 20 or up to 10 molecules of thyroid hormone analogues conjugated per nanoparticle. By way of non-limiting example, the ratio of the thyroid hormone analogues or other therapeutic molecules per nanoparticle may range from a ratio of 1 thyroid hormone analogue molecule per 1 nanoparticle (shown also as 1:1) up to 100 thyroid hormone analogues per nanoparticle (shown also as 100:1). More preferably, the range may be from 10:1-50:1 (i.e., 10:1, 20:1, 30:1, 40:1) thyroid hormones or thyroid hormone analogues or other therapeutic molecules per nanoparticle. In other embodiments, the ratio of conjugated thyroid hormone analogues may range from 10:1-50:1, 30:1-40:1, 20:1-25:1 or 10:1-20:1 thyroid hormone analogue molecules per nanoparticle. In various embodiments, the density of the thyroid hormone analogues in the nanoparticles is between 0.1 and 25%, for example the density of the thyroid hormone analogue particle may be between approximately 0.1-1%, 0.5-2%, 1-3%, 2-5%, 3-7%, 4-10%, 5-15%, 7-20%, 0.2-25%, 0.5-20%, 1-20% or 1-15%.

In some embodiments, the nanoparticles within the present disclosure may include up to approximately 100, up to 90, up to 80, up to 70, up to 60, up to 50, up to 40 up to 30, up to 20 or up to 10 molecules of anti-inflammatory agents per nanoparticle. By way of non-limiting example, the ratio of the anti-inflammatory or other agents per nanoparticle may range from a ratio of 1 anti-inflammatory molecule per 1 nanoparticle (shown also as 1:1) up to 100 anti-inflammatory agent molecules per nanoparticle (shown also as 100:1). More preferably, the range may be from 10:1-30:1 (i.e., 10:1-30:1) anti-inflammatory agents or other therapeutic molecules per nanoparticle. In other embodiments, the ratio of anti-inflammatory agents may range from 10:1-50:1, 30:1-40:1, 20:1-25:1 or 10:1-20:1 anti-inflammatory agents per nanoparticle. In various embodiments, the density of the anti-inflammatory agent in the nanoparticles may be between 0.1 and 25%, for example the density of the anti-inflammatory agent may be between approximately 0.1-1%, 0.5-2%, 1-3%, 2-5%, 3-7%, 4-10%, 5-15%, 7-20%, 0.2-25%, 0.5-20%, 1-20% or 1-15%. In some embodiments, the anti-inflammatory agent may include at least 10 molecules of anti-inflammatory agent per nanoparticle or microparticle polymer. For example, the polymeric particle may encapsulate at least 10, at least 20, at least 30, at least 40, at least 50, at least 100, at least 200, at least 500 anti-inflammatory molecules per nanoparticle.

In some embodiments, the anti-inflammatory NSAIDs may be administered at any known therapeutic concentration. For example, therapeutic concentrations may be approximately 50 µg-2000 mg/day. The concentration and effective dose may vary depending on the NSAID being encapsulated. For example, the concentration may vary between 50-200 µg/day, 200-500 µg/day, 500-1000 µg/day, 1-50 mg/day, 50-100 mg/day, 100-200 mg/day, 200-400 mg/day, 400-800 mg/day, 800-1000 mg/day or 1000-2000 mg/day. In some embodiments, the NSAID dose or payload may be administered between 1-1000 mg, 1-500 mg, 1-100 mg, 1-50 mg or 1-10 mg. In other embodiments, the dose may be significantly lower and may range from 50-100 µg, 50-500 µg, or 50-1000 µg.

Embodiments, of the thyroid hormone analogues that may include salicylates encapsulated by the polymeric particles, may be administered at any known therapeutic concentration. For example, salicylates may be administered at a therapeutic concentration between approximately 50 µg-6000 mg/day. The concentration and effective dose may vary depending on the salicylate being encapsulated and administered. For example, the concentration may vary between 50-200 µg/day, 200-500 µg/day, 500-1000 µg/day, 1-50 mg/day, 50-100 µg/day, 100-200 mg/day, 200-400 mg/day, 400-800 mg/day, 800-1000 mg/day, 1000-2000 mg/day, 2000-3500 mg/day, 3500-5000 mg/day or 5000-6000 mg/day. In some embodiments, the dose or payload of salicylates may be administered between 1-1000 mg, 1-500 mg, 1-100 mg, 1-50 mg or 1-10 mg. In other embodiments, the dose may be significantly lower and range from 50-100 µg, 50-500 µg, or 50-1000 µg.

Embodiments, of the thyroid hormone analogues that may include anti-inflammatory glucocorticoids encapsulated by the polymeric particles, may be administered at any known therapeutic concentration. For example, anti-inflammatory glucocorticoids may be administered at a therapeutic concentration between approximately 1 µg-100 mg/day. The concentration and effective dose may vary depending on which anti-inflammatory glucocorticoids is being encapsulated and administered. For example, the concentration may vary between 1-50 µg/day, 50-100 µg/day, 100-500 µg/day, 500-1000 µg/day, 1-5 mg/day, 5-10 mg/day, 10-20 mg/day, 20-25 mg/day, or 25-30 mg/day, 30-100 mg/day. In some embodiments, the dose or payload of anti-inflammatory glucocorticoids may be administered between 1-100 mg, 1-50 mg, or 1-10 mg. In other embodiments, the dose may be significantly lower and range from 50-100 µg, 50-500 µg, or 50-1000 µg.

In some embodiments that include anti-oxidant polyphenols encapsulated by the polymeric particles, the anti-oxidant polyphenols may be administered at any known therapeutic concentration. The therapeutic concentration of the encapsulated anti-oxidant polyphenols may vary from 1 µg-5000 mg/day depending on the anti-oxidant polyphenol being administered. For example, the anti-oxidant polyphenol may be administered in therapeutic concentration between approximately 1-50 µg/day, 50-100 µg/day, 100-500 µg/day, 500-1000 µg/day, 1-100 mg/day, 100-300 mg/day, 300-600 mg/day, 600-800 mg/day, 800-1000 mg/day, 1000-2000 mg/day, 2000-3500 mg/day or 3500-5000 mg/day. In some embodiments, the dose or payload of anti-oxidant polyphenols may be administered between 1-5000 mg, 1-3000 mg, 1-1000 mg, 1-500 mg, 1-100 mg, 1-50 mg or 1-10 mg. In other embodiments, the dose may be significantly lower and range from 1-50 µg, 50-100 µg, 50-500 µg, or 50-1000 µg.

Embodiments including anti-fibrotic agents having anti-inflammatory properties encapsulated by the conjugated thyroid hormone analogue may be administered at a dose between 1 mg-3500 mg/day. For example, the anti-fibrotic agent may be administered in therapeutic concentration between approximately 1-50 mg/day, 50-100 mg/day, 100-500 mg/day, 500-1000 mg/day, 1000-2000 mg/day or 2000-3500 mg/day. In some embodiments, the dose or payload of anti-fibrotic agents having anti-inflammatory properties may be administered between 1-3500 mg, 1-3000 mg, 1-1000 mg, 1-500 mg, 1-100 mg, 1-50 mg or 1-10 mg. In other embodiments, the dose may be significantly lower and range from 1-50 µg, 50-100 µg, 50-500 µg, or 50-1000 µg.

Embodiments including anti-CD47 antibodies encapsulated by the conjugated thyroid hormone analogue may be administered at a dose between 1 µg/day-500 mg/day. For example, the anti-CD47 antibody may be administered in therapeutic concentration between approximately 1-50 µg/day, 50-100 µg/day, 100-500 µg/day, 500-1000 µg/day, 1-200 mg/day or 200-500 mg/day. In some embodiments, the dose or payload of the anti-CD47 antibody may be administered between 1 µg-500 mg, 1-30 µg, 1-100 µmg, 1-500 µg, 500-1000 µg, 1-100 mg, 1-50 mg or 1-10 mg.

The use of the encapsulation into the conjugated thyroid hormone analogue and precise targeting of the anti-inflammatory agent to the inflammation site produces unexpected results in the therapeutic dose administered to control, reduce or suppress the inflammation. The encapsulation of the anti-inflammatory agent in the polymer may allow for lower doses of the anti-inflammatory agent to be administered than in a situation wherein the anti-inflammatory were administered on its own. In particular, doses administered between 1 µg-100 mg or 1 mg-100 mg of the encapsulated anti-inflammatory may be significantly less than the therapeutic dose administered without being encapsulated. For example, a common NSAID such as Ibuprofen may have a therapeutic dose that is 200-600 mg when administered without targeted administration in the encapsulated polymer. When encapsulated, the ibuprofen may reduce inflammation in extremely low doses between 1-100 mg, which is between 16-50% of the therapeutic dose when 100 mg is administered and 0.2-0.5% of the typical therapeutic dose when 1 mg is administered. Ultimately, lowered doses may mean less toxicity and adverse side effects. For instance, in the case of ibuprofen, decreased instances of ulcers, bleeding, headaches, nausea, diarrhea, abdominal pain etc.

The conjugated thyroid hormone analogue may be administered with one or more pharmaceutically acceptable carriers. "Pharmaceutically acceptable carriers" may refer to and include any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

In some embodiments, the conjugated thyroid hormone analogue, encapsulating one or more additional agents may be administered directly into the site of inflammation. For example, the composition may be injected into inflamed joints and muscles. In other embodiments, the conjugated thyroid hormone analogue may be formulated for administration via one or more of the following routes, including but not limited to parenteral including via catheterization, intravenous, oral, rectal, topical such as a Band-Aid, cream, ointment or a gauze pad, ophthalmic, local implantation, subcutaneous, intramolecular, intraperitoneal, intramuscular, buccal, vaginal, intraorbital, intracerebral, intracranial, intraspinal, intraventricular, intrathecal, intracisternal, intracapsular, intranasal or by aerosol administration or a combination of routes thereof.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

In some embodiments, a medical device may be coated with the conjugated thyroid hormone analogue wherein the polymer has encapsulated at least one additional anti-inflammatory agent. The coated medical device may include stents, catheters, cannulas or electrodes.

In another embodiment, conjugated thyroid hormone analogues may further encapsulate one or more nerve growth factors or other neurogenesis factors useful to protect against damage associated with the body's immune/inflammatory response to an initial injury to nerve tissue. Such a response may follow trauma to nerve tissue, caused, for example, by an autoimmune dysfunction, neoplastic lesion, infection, chemical or mechanical trauma, disease, by interruption of blood flow to the neurons or glial cells, or by other trauma to the nerve or surrounding material. For example, the primary damage results from hypoxia or ischemia-reperfusion following occlusion of a neural blood supply, as in an embolic stroke, is believed to be immunologically associated. In addition, at least part of the damage associated with a number of primary brain tumors also appears to be immunologically related. Application of a polymeric thyroid hormone analogue alone or in combination with nerve growth factors or other neurogenesis factors, either directly or systemically alleviates and/or inhibits the immunologically related response to a neural injury.

Alternatively, administration of an agent capable of stimulating the expression and/or secretion in vivo of conjugated thyroid hormone analogues alone or in combination with nerve growth factors or other neurogenesis factors expression, preferably at the site of injury, may also be used. Where the injury is to be induced, such as during surgery or other aggressive clinical treatment, the conjugated thyroid hormone analogues alone or in combination with nerve growth factors or other neurogenesis factors or agent may be provided prior to induction of the injury to provide a neuroprotective effect to the nerve tissue at risk.

In some embodiments, the conjugated thyroid hormone analogue, including one or more additionally encapsulated agents may be encapsulated into a hydrogel for local implantation into the inflammation site. Synthetic hydrogels from methacrylate derived polymers may be used in biomedical applications because of their similarity to the living tissues. The most widely used synthetic hydrogels are polymers of acrylic acid, acrylamide and 2-hydroxyethyl methacrylate (HEMA). The poly HEMA may be inexpensive, biocompatible, available primary alcohol side chain elongation functionality for conjugation and fit for ocular, intraocular and other ophthalmic applications which make them perfect drug delivery materials. The poly HEMA may be immune to cell attachment and provides zero cell motility which makes them an ideal candidate for internal delivery system. In one example, formulations of a hydrogel may include biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades.

In addition to the aforementioned ingredients, formulations of the conjugated thyroid hormone analogue may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants), excipients, dispersing agents; inert diluents, granulating and disintegrating agents, sweetening agents, coloring agents, physiologically degradable compositions such as gelatin; aqueous vehicles and solvents; oily vehicles and solvents; dispersing or wetting agents; emulsifying agents, demulcents, buffers, salts, fillers, emulsifying agents, antioxidants, antibiotics, antifungal agents, stabilizing agents, and pharmaceutically acceptable polymeric or hydrophobic materials and the like.

In an alternative embodiment, the release of a conjugated thyroid hormone analogue encapsulating one or more additional agent inside the polymer, may be controlled by further encapsulating the polymer itself within a liposome, microparticle, or nanoparticle. The breakdown of the liposome, microparticle or nanoparticle may be calculated to further control length of time wherein the conjugated thyroid hormone analogue is released at the site of inflammation. This embodiment may include prolonged release times of the conjugated thyroid hormone between approximately 1-72 hours, 10-60 hours, 15-50 hours, 20 to 40 hours or for 24 hours.

Embodiments of the conjugated thyroid hormone analogue may further be applied toward embodiments of methods for treating inflammatory conditions. Inflammatory conditions that may be treated may include but is not limited to Parkinson's disease, trauma, cerebral ischemia, amyotrophic lateral sclerosis, multiple sclerosis, arthritis, myositis, poikiloderma, rosacea, psoriasis, acne, pityriasis rosea, eczema, and a combination of inflammatory conditions thereof. Furthermore, embodiments of the method for treating an inflammatory condition may further include treating musculoskeletal conditions that may or may not include inflammation. The musculoskeletal condition may include conditions such as aches and pains that are in the body's muscles, joints, tendons, ligaments, nerves, and combination of musculoskeletal conditions thereof.

In one embodiment, the steps for treating an inflammatory condition may include conjugating an anti-angiogenic thyroid hormone analogue such as tetrac or triac to a polymer where the results of the conjugation may form a conjugated thyroid hormone analog. Embodiments of methods for treating an inflammatory condition may further comprise encapsulating inside the polymer of the conjugated thyroid hormone analog, at least one of the following, including but not limited to at least one NSAID, at least one salicylate, at least one anti-inflammatory glucocorticoid, an anti-fibrotic agent having anti-inflammatory properties such as pirfenidone or a combination of anti-inflammatory agents. Embodiments of the method may also include binding the conjugated thyroid hormone analog, with or without the presence of an additional agent encapsulated within the polymer, to one or more of the following inflammation modulating receptors such as cytokine receptors, interleukin receptors chemokine receptors or a combination of receptors thereof.

Embodiments of the method for treating an inflammatory condition my further comprise the additional step of encapsulating the polymer inside a liposome, microparticle or nanoparticle for example in an effort to control the release of the conjugated thyroid hormone analogue. In some embodiments, the liposome or microparticle can be lodged in capillary beds surrounding ischemic tissue, or applied to the inside of a blood vessel via a catheter.

Moreover, the method for treating one or more inflammatory conditions may also include the additional step of administering the conjugated thyroid hormone analog, with or without the additional encapsulated anti-inflammatory agent, at a therapeutic concentration between approximately 200 μg/day to approximately 1000 mg. In some embodiments the dose administered may be less than 1000 mg/day, less than 500 mg/day, less than 200 mg/day, less than 50 mg/day, less than 2000 μg/day, less than 1500 μg/day, less than 1000 μg/day, less than 500 μg/day or less than 200 μg/day. The dosage administered may vary depending on dosing factors known to those skilled in the art. The period of dosing may vary depending on the dosing amount being administered. The step of administering may be performed at a specific interval of time, for example, the step of administration may occur at an interval of once a week, once per day (i.e. every 24 hours), once every other day (i.e. every 48 hours), once every three days (i.e. every 72 hours) or twice a day or more.

The step of administering the conjugated thyroid hormone, with or without the additional encapsulated anti-inflammatory agent may occur topically, parenterally, locally at the site of inflammation, systemically by injectable routes such as subcutaneous, intravenous, intraperitoneal, intramuscular, intracerebral, intraorbital, intracranial, intraspinal, intraventricular, intrathecal, intracisternal, intracapsular, or by catheterization, orally, rectally, ophthalmically, local implantation, buccal, vaginal, intranasal or by aerosol administration or a combination of routes thereof.

While this disclosure has been described in conjunction with the specific embodiments outlined above, it is evident that many alternatives, modifications and variations will be apparent to those skilled in the art. Accordingly, the embodiments of the disclosure as set forth above are intended to be illustrative, not limiting. Various changes may be made without departing from the spirit and scope of the invention as defined in the following claims. The claims provide the scope of the coverage of the invention and should not be limited to the specific examples provided herein.

What is claimed:

1. A composition comprising:
    a thyroid hormone analogue conjugated to a polymer, wherein the thyroid hormone analogue is immobilized to a surface of the polymer, wherein said thyroid hormone analogue targets integrin αvβ3; and
    at least one anti-inflammatory agent encapsulated by the polymer, wherein said at least one anti-inflammatory agent is selected from a non-steroidal anti-inflammatory drug (NSAID), a tyrosine kinase inhibitor, a salicylate, an anti-inflammatory glucocorticoid and an anti-fibrotic agent having anti-inflammatory properties.

2. The composition of claim 1, wherein the thyroid hormone analogue is at least one of tetraiodothyroacetic acid (tetrac) and triiodothyroacetic acid (triac).

3. The composition of claim 1, wherein the polymer is selected from the group consisting of polylactic acid (PLLA), polyglycolic acid (PGA), polyacrylic acid, poly(lactic-co-glycolic acid) (PLGA), polyethylene glycol (PEG), poly-L-lysine, chitosan, hyaluronic acid, fatty acids, polyamine, co-polymers thereof and combinations thereof.

4. The composition of claim 1, wherein the polymer is formulated into a nanoparticle.

5. The composition of claim 1, wherein the NSAID is selected from the group consisting of ibuprofen, diclofenac, indomethacin, ketoprofen, naproxen, sulindac, celecoxib, nabumetone, mefenamic acid, oxyphenbutazone, and combinations thereof.

6. The composition of claim 1, further comprising an anti-oxidant polyphenol encapsulated within the polymer.

7. The composition of claim 6, wherein the anti-oxidant polyphenol is at least one of a flavone, an isoflavone, and a flavonoid.

8. The composition of claim 7, wherein the flavonoid is selected from the group consisting of resveratrol, quercetin, myricetin, catechin, epigallocatechin, genistein and combinations thereof.

9. The composition of claim 4, wherein the nanoparticle has a diameter between approximately 10 nm and <1000 nm.

10. The method of claim 1, wherein the anti-fibrotic agents having anti-inflammatory properties is pirfenidone.

11. The composition of claim 1, further comprising one or more bisphosphonates encapsulated in the polymer.

12. The composition of claim 11, wherein the one or more bisphosphonates are selected from the group consisting of risendronate, alendronate, ibandronate, etidronate, pamidronate, tiludronate, and zoledronic acid.

13. The composition of claim 1, wherein the composition is formulated into a hydrogel.

14. A method for making the composition of claim 1 comprising the steps of:
    conjugating a thyroid hormone analogue to a polymer, forming a conjugated thyroid hormone analog; and
    encapsulating inside the polymer of the conjugated thyroid hormone analogue at least one of a non-steroidal anti-inflammatory drug (NSAID), a salicylate, an anti-inflammatory glucocorticoid and an anti-fibrotic agent having anti-inflammatory properties.

15. The method of claim 14, wherein the step of encapsulating includes encapsulating the at least one of the non-steroidal anti-inflammatory drug (NSAID), the salicylate, the anti-inflammatory glucocorticoid and the anti-fibrotic agent having anti-inflammatory properties at a dose between 1.0-100 mg.

16. The method of claim 14, further comprising the step of encapsulating the polymer in a liposome, microparticle or nanoparticle.

17. The method of claim 14, wherein the NSAID is selected from the group consisting of ibuprofen, diclofenac, indomethacin, ketoprofen, naproxen, sulindac, celecoxib, nabumetone, mefenamic acid, oxyphenbutazone, and combinations thereof.

18. The method of claim 14, further comprising the step of encapsulating at least one anti-oxidant polyphenol inside the polymer, wherein the anti-oxidant polyphenol is at least one of a flavone, an isoflavone, and a flavonoid.

19. The method of claim 18, wherein the flavonoid is selected from the group consisting of resveratrol, quercetin, myricetin, catechin, epigallocatechin, enistein and combinations thereof.

20. The method of claim 14, wherein the polymer is selected from the group consisting of polylactic acid (PLLA), polyglycolic acid (PGA), polyacrylic acid, polyethylene glycol (PEG), poly-L-lysine, chitosan, hyaluronic acid, fatty acids, polyamine, co-polymers thereof and combinations thereof.

21. A method comprising administering the composition of claim 1 to a subject.

22. The method of claim 21, wherein the step of administering is performed at an interval selected from the group consisting of once a day, every other day and once a week.

23. The method of claim 21, wherein the step of administering occurs topically, systemically, orally, locally at the site of inflammation, and a combination thereof.

* * * * *